US010851400B2

(12) United States Patent
Bicker et al.

(10) Patent No.: US 10,851,400 B2
(45) Date of Patent: Dec. 1, 2020

(54) ASSAY FOR HIGH-THROUGHPUT IDENTIFICATION OF THERAPEUTIC COMPOUNDS

(71) Applicants: Kevin L. Bicker, Rockvale, TN (US);
Kevin J. Fisher, Collierville, TN (US);
Ashley E. Corson, Greenbrier, TN (US)

(72) Inventors: Kevin L. Bicker, Rockvale, TN (US);
Kevin J. Fisher, Collierville, TN (US);
Ashley E. Corson, Greenbrier, TN (US)

( * ) Notice: Subject to any disclaimer, the term of this patent is extended or adjusted under 35 U.S.C. 154(b) by 391 days.

(21) Appl. No.: 15/464,043

(22) Filed: Mar. 20, 2017

(65) Prior Publication Data

US 2017/0268032 A1    Sep. 21, 2017

Related U.S. Application Data

(60) Provisional application No. 62/310,746, filed on Mar. 20, 2016.

(51) Int. Cl.
*C12Q 1/18* (2006.01)
*C12N 15/10* (2006.01)
(Continued)

(52) U.S. Cl.
CPC ............... *C12Q 1/18* (2013.01); *C07K 17/06* (2013.01); *C07K 17/08* (2013.01);
(Continued)

(58) Field of Classification Search
CPC ...... C12Q 1/18; C12N 15/1065; C07K 17/06; C07K 17/08
See application file for complete search history.

(56) References Cited

U.S. PATENT DOCUMENTS 5,166,321 A    11/1992    Lai et al.
5,886,104 A    3/1999    Pedersen et al.
(Continued)

FOREIGN PATENT DOCUMENTS

WO    WO 2014/171899 A1    10/2014
WO    WO 2014/193973 A2    12/2014

OTHER PUBLICATIONS

Lebl et al. (Int. J. Peptide Protein Res., 1993, 41:201-203) (Year: 1993).*

(Continued)

*Primary Examiner* — Jeremy C Flinders
(74) *Attorney, Agent, or Firm* — Baker Donelson

(57) ABSTRACT

A solid supported branched linker assay system, including an alpha compound and a beta compounds reversibly tethered to a solid support; a branched linker coupled to the solid support that tethers the alpha and beta compounds to the solid support; the branched linker having two cleavable linkers that are chemically distinct from one another, wherein a first chemically distinct linker tethers the β compound to the branched linker and a second chemically distinct linker tethers the α compound to the branched linker; and at least two means for cleaving the chemically distinct linkers, wherein a first cleavage means is configured to selectively cleave a first chemically distinct linker and a second cleavage means is configured to selectively cleave a second chemically distinct linker.

8 Claims, 26 Drawing Sheets

(51) Int. Cl.
C07K 17/06 (2006.01)
C07K 17/08 (2006.01)
C07K 5/083 (2006.01)
C07K 5/087 (2006.01)

(52) U.S. Cl.
CPC ........ *C12N 15/1065* (2013.01); *C07K 5/0806* (2013.01); *C07K 5/0812* (2013.01); *G01N 2333/195* (2013.01); *G01N 2500/10* (2013.01)

(56) References Cited

U.S. PATENT DOCUMENTS

| | | |
|---|---|---|
| 2008/0248483 A1 | 10/2008 | Palsson |
| 2010/0029911 A1 | 2/2010 | Frank et al. |
| 2012/0178086 A1 | 7/2012 | Franzini et al. |
| 2013/0267457 A1 | 10/2013 | Llano-Sotelo et al. |
| 2015/0314014 A1 | 11/2015 | Lauermann |
| 2016/0075734 A1 | 3/2016 | Menegatti |

OTHER PUBLICATIONS

Simpson et al. (Tetrahedron Letters, 2012, 53:2341-2344) (Year: 2012).*
Lack et al. (Helvetica Chimica Acta, 2002, 85:495-501) (Year: 2002).*
Silen et al. (Antimicrobial Agents and Chemotherapy, 1998, 42(6):1447-1453) (Year: 1998).*
Ni et al. (J. Med. Chem., 1996, 39(8):1601-1608) (Year: 1996).*
Sizemore et al. (Protein and Peptide Letters, 1996, 3(4):253-260) (Year: 1996).*
International Searching Authority, International Search Report for PCT/US2017/023236, dated Jun. 15, 2017 (attached hereto).
W.H.O., Antimicrobial Resistance: Report on Global Surveillance. World Health Organization; France: 2014.
Welcome Trust and UK Government, Antimicrobial Resistance: Tackling a Crisis for the Health and Wealth of Nations. The Review on Antimicrobial Resistance; London: 2014 (Jim O'Neal, Chair).
Tenover, Mechanisms of Antimicrobial Resistance in Bacteria. Am J Med. 2006; 119(6):S3-S10.
Blair et al., Molecular mechanisms of antibiotic resistance. Nat Rev Microbiol. 2015; 13:42-51.
Brogden, Antimicrobial peptides: pore formers or metabolic inhibitors in bacteria? Nat Rev Microbiol. 2005; 3:238-250.
Zasloff, Antimicrobial peptides of multicellular organisms. Nature. 2002; 415(6870):389-95.
Jensenn et al., Peptide Antimicrobial Agents. Clin Microbiol Rev. 2006; 19(3):491-511.
Hancock and Sahl, Antimicrobial and host-defense peptides as new anti-infective therapeutic strategies. Nat Biotechnol. 2006; 24(12):1551-7.
Culf and Ouellette, Solid-phase synthesis of N-substituted glycine oligomers (alpha-peptoids) and derivatives. Molecules. 2010; 15(8):5282-335.
Giuliani & Rinaldi, Beyond natural antimicrobial peptides: multimeric peptides and other peptidomimetic approaches. Cell Mol Life Sci. 2011; 68(13):2255-66.
Zuckermann et al., Efficient method for the preparation of peptoids [oligo (N-substituted glycines)] by submonomer solid-phase synthesis, (1992).

Chongsiriwatana et al., Functional synergy between antimicrobial peptoids and peptides against Gram-negative bacteria. Antimicrob Agents Chemother. 2011; 55(11):5399-402.
Kapoor et al., Efficacy of antimicrobial peptoids against *Mycobacterium tuberculosis*. Antimicrob Agents Chemother. 2011; 55(6):3058-62.
Kapoor et al., Antimicrobial peptoids are effective against Pseudomonas aeruginosa biofilms. Antimicrob Agents Chemother. 2011; 55(6):3054-7.
Chongsiriwatana et al., Peptoids that mimic the structure, function and mechanism of helical antimicrobial peptides. Proc Natl Acad Sci U S A. 2008; 105(8):2794-9.
Patch JA, Barron AE. Helical peptoid mimics of magainin-2 amide. J Am Chem Soc. 2003; 125(40):12092-3.
Hein-Kristensen et al., Bacterial membrane activity of alpha-peptide/beta-peptoid chimeras: Influence of amino acid composition and chain length on the activity against different bacterial strains. BMC Microbiol. 2011; 11:144.
Kennedy et al., Application of Combinatorial Chemistry Science on Modern Drug Discovery. J Comb Chem. 2008; 10(3):345-354.
Lam & Krchnak, The "One-Bead-One-Compound" Combinatorial Library Method. Chem Rev. 1997; 97(2):411-448.
Figliozzi, GM.; Goldsmith, R.; Ng, SC.; Banville, SC.; Zuckermann, RN. Methods of Enzymology. vol. 267. Academic Press; 1996. Synthesis of N-substituted glycine peptoid libraries; p. 437-447.
Udugamasooriya DG, Dineen SP, Brekken RA, Kodadek T. A Peptoid "Antibody Surrogate" That Antagonizes VEGF Receptor 2 Activity. J Am Chem Soc. 2008; 130(17):5744-5752.
Gao Y, Kodadek T. Synthesis, Screening and Hit Optimization of Stereochemically Diverse Combinatorial Libraries of Peptide Tertiary Amides. Chem Biol. 2013; 20(3):360.
Fluxa VS, Maillard N, Page MGP, Reymond J-L. Bead diffusion assay for discovering antimicrobial cyclic peptides. Chem Commun. 2011; 47(5):1434-1436.
Oldenburg KR, Vo KT, Ruhland B, Schatz PJ, Yuan Z. A Dual Culture Assay for Detection of Antimicrobial Activity. J Biomol Screening. 1996; 1(3):123-130.
Silen JL, Lu AT, Solas DW, Gore MA, Maclean D, Shah NH, Coffin JM, Bhinderwala NS, Wang Y, Tsutsui KT, Look GC, Campbell DA, Hale RL, Navre M, DeLuca-Flaherty CR. Screening for Novel Antimicrobials from Encoded Combinatorial Libraries by Using a Two-Dimensional Agar Format. Antimicrob Agents Chemother. 1998; 42(6):1447-1453.
Chen X, Tan PH, Zhang Y, Pei D. On-Bead Screening of Combinatorial Libraries: Reduction of Nonspecific Binding by Decreasing Surface Ligand Density. J Comb Chem. 2009; 11(4):604-611.
Kappel J, Barany G. Methionine anchoring applied to the solid-phase synthesis of lysine-containing "head-to-tail" cyclic peptides. Lett Pept Sci. 2003; 10(2):119-125.
Chongsiriwatana NP, Miller TM, Wetzler M, Vakulenko S, Karlsson AJ, Palecek SP, Mobashery S, Barron AE. Short Alkylated Peptoid Mimics of Antimicrobial Lipopeptides. Antimicrob Agents Chemother. 2011; 55(1):417-420.
Mojsoska B, Zuckermann RN, Jenssen Hv. Structure-Activity Relationship Study of Novel Peptoids That Mimic the Structure of Antimicrobial Peptides. Antimicrob Agents Chemother. 2015; 59(7):4112-4120.
Pendleton et al., Clinical relevance of the ESKAPE pathogens. Expert Rev Anti-Infect Ther. 2013; 11(3):297-308.
Fisher et al., Peptiod Library Agar Diffusion (PLAD) Assay for teh High-Throughput Identification of Antimicrobial Peptides. ACS Comb. Sci. 2016; 18(6):287-291.

\* cited by examiner

PLAD Linker

Screening

Peptoid Sequencing

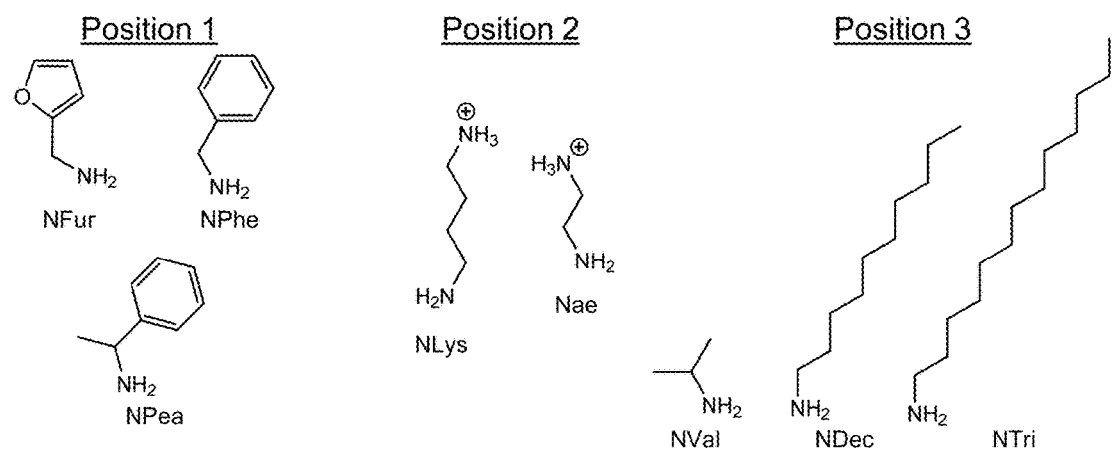
Figure 10A
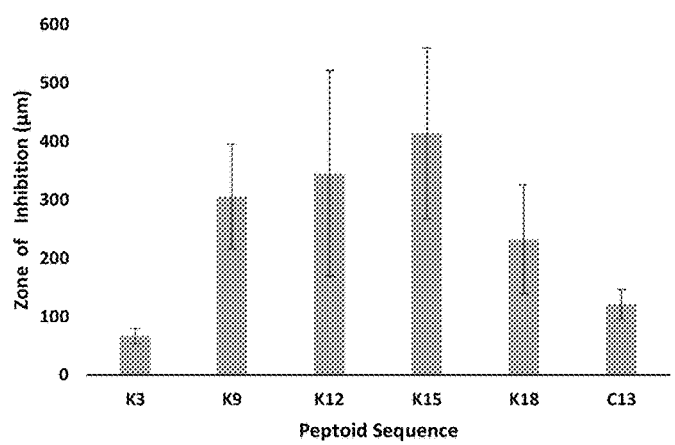
Figure 10B
| Bacteria | MIC (μg/mL) |
|---|---|
| Enterococcus faecalis | 50 |
| Enterococcus faecium | 25 |
| Staphylococcus aureus | 50 |
| Klebsiella pneumoniae | >100 |
| Acinetobacter baumannii | 25 |
| Pseudomonas aeruginosa | 100 |
| Escherichia coli | 100 |
Figure 10C

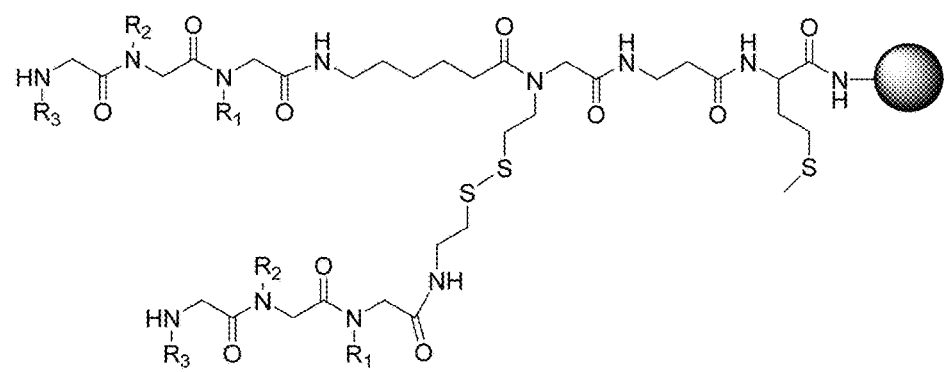
Position 1
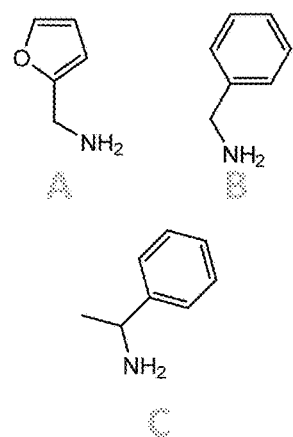
Position 2
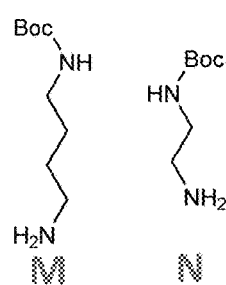
Position 3
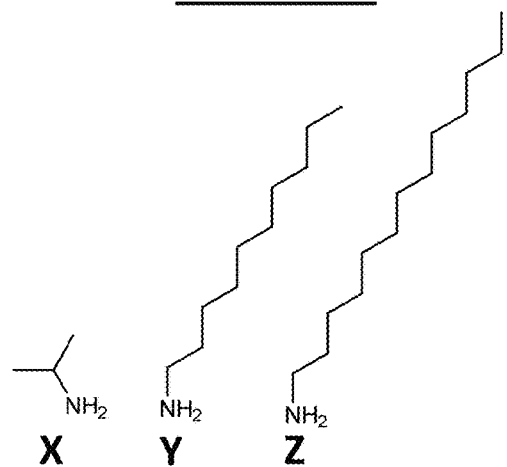
Figure 13

|  | C | Position |  | N |
|---|---|---|---|---|
| Sequence | 1 | 2 | 3 | MS MW (da) |
| KJF1 | Nfur | Ndab | Nval | 739 |
| KJF2 | Nfur | Ndab | Ndec | 837 |
| KJF3 | Nfur | Ndab | Ntri | 879 |
| KJF4 | Nfur | Nlys | Nval | 767 |
| KJF5 | Nfur | Nlys | Ndec | 865 |
| KJF6 | Nfur | Nlys | Ntri | 907 |
| KJF7 | Nphe | Ndab | Nval | 749 |
| KJF8 | Nphe | Ndab | Ndec | 847 |
| KJF9 | Nphe | Ndab | Ntri | 889 |
| KJF10 | Nphe | Nlys | Nval | 777 |
| KJF11 | Nphe | Nlys | Ndec | 875 |
| KJF12 | Nphe | Nlys | Ntri | 917 |
| KJF13 | Nspe | Ndab | Nval | 763 |
| KJF14 | Nspe | Ndab | Ndec | 861 |
| KJF15 | Nspe | Ndab | Ntri | 903 |
| KJF16 | Nspe | Nlys | Nval | 791 |
| KJF17 | Nspe | Nlys | Ndec | 889 |
| KJF18 | Nspe | Nlys | Ntri | 931 |

Figure 20

|               |           |          | C    | Position | N    |
|---------------|-----------|----------|------|----------|------|
| Hit Identifier | MS MW (da) | Sequence | 1    | 2        | 3    |
| KJF150        | 931       | K18      | NPea | NLys     | NTri |
| KJF151        | 903       | K15      | NPea | NDab     | NTri |
| KJF154        | 917       | K12      | NPhe | NLys     | NTri |
| KJF155        | 931       | K18      | NPea | NLys     | NTri |
| KJF156        | 889       | K9       | NPhe | NDab     | NTri |
| KJF157        | 917       | K12      | NPhe | NLys     | NTri |
| KJF158        | 889       | K9       | NPhe | NDab     | NTri |
| KJF159        | 879       | K3       | NFur | NDab     | NTri |
| KJF160        | 931       | K18      | NPea | NLys     | NTri |
| KJF161        | 917       | K12      | NPhe | NLys     | NTri |
| KJF162        | 931       | K18      | NPea | NLys     | NTri |
| KJF163        | 889       | K9       | NPhe | NDab     | NTri |
| KJF164        | 903       | K15      | NPea | NDab     | NTri |
| KJF165        | 931       | K18      | NPea | NLys     | NTri |
| KJF166        | 903       | K15      | NPea | NDab     | NTri |
| KJF167        | 917       | K12      | NPhe | NLys     | NTri |
| KJF168        | 889       | K9       | NPhe | NDab     | NTri |
| KJF169        | 903       | K15      | NPea | NDab     | NTri |
| KJF170        | 917       | K12      | NPhe | NLys     | NTri |
| KJF171        | 879       | K3       | NFur | NDab     | NTri |
| KJF172        | 917       | K12      | NPhe | NLys     | NTri |
| KJF173        | 917       | K12      | NPhe | NLys     | NTri |
| KJF174        | 917       | K12      | NPhe | NLys     | NTri |
| KJF175        | 889       | K9       | NPhe | NDab     | NTri |
| KJF176        | 889       | K9       | NPhe | NDab     | NTri |
| KJF177        | 931       | K18      | NPea | NLys     | NTri |
| KJF178        | 889       | K9       | NPhe | NDab     | NTri |
| KJF179        | 903       | K15      | NPea | NDab     | NTri |
| KJF180        | 889       | K9       | NPhe | NDab     | NTri |
| KJF181        | 931       | K18      | NPea | NLys     | NTri |
| KJF183        | 931       | K18      | NPea | NLys     | NTri |

Figure 24

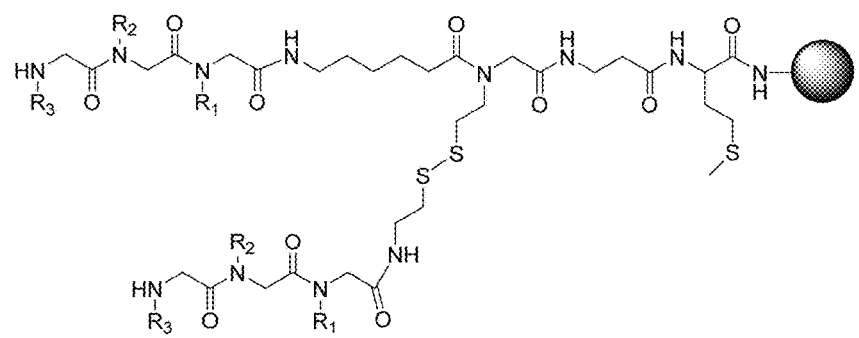
Figure 25A
Position 1  Position 2  Position 3
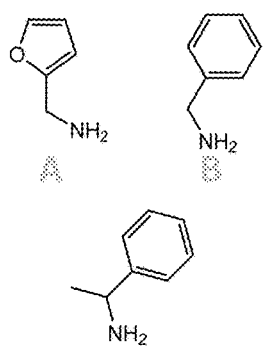 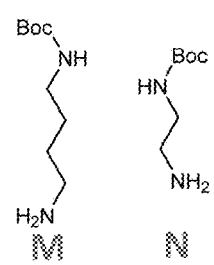 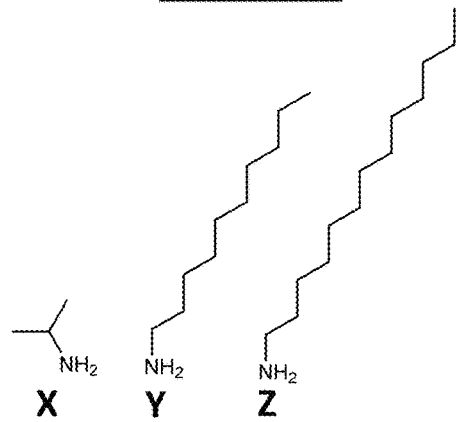
Figure 25B
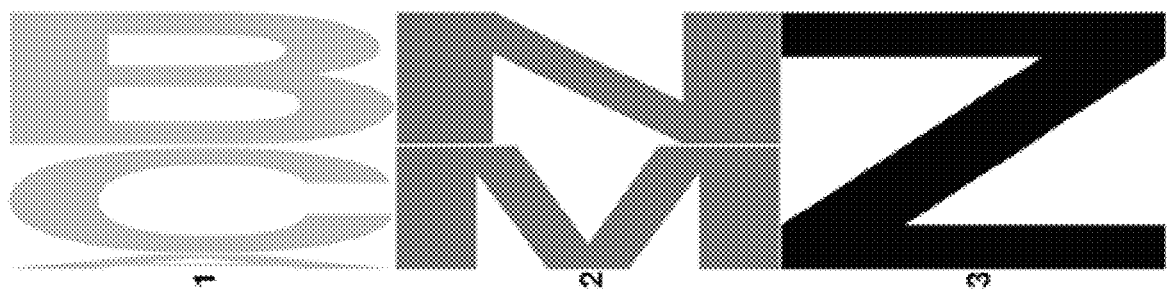
Figure 25C

ASSAY FOR HIGH-THROUGHPUT IDENTIFICATION OF THERAPEUTIC COMPOUNDS

CROSS REFERENCE TO RELATED APPLICATIONS

This application claims the benefit of U.S. Provisional Application No. 62/310,746 entitled "Peptoid Library Agar Diffusion Assay for High-Throughput Identification of Antimicrobial Compounds" and filed on 20 Mar. 2016, the contents of which are incorporated by reference in its entirety.

GOVERNMENT INTERESTS

This invention was made with government support under Grant No. R03 AI112861 awarded by the National Institutes of Health. The government has certain rights in the invention.

All patents, patent applications, and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

FIELD OF THE INVENTION

In various exemplary embodiments, the present invention comprises a solid supported branched linker system and high-throughput screening method for the identification of therapeutic compounds.

BACKGROUND OF THE INVENTION

The increasing prevalence of multi-drug-resistant (MDR) bacterial infections in the clinic necessitates methods to rapidly identify potent new antimicrobial agents that are effective against MDR bacteria. Antimicrobial resistance (AMR) is considered by the World Health Organization (WHO) to be a major threat to global public health, resulting in significant detrimental effects on mortality rates and economic growth due to the growing cost of bacterial infection treatment. A recent study predicted that the by the year 2050, AMR will result in 10 million premature deaths per year worldwide and roughly $100 trillion USD in lost economic output. Bacterial resistance is a growing problem due to increasing and improper use of antibiotics combined with the ability of bacteria to readily transmit information from one microbe to another. Common mechanisms of bacterial resistance include drug efflux pumps and enzymes that break down common antibiotics, such as β-lactamases and aminoglycosides. Although there is a prevalent AMR problem, relatively few bioavailable antimicrobial therapeutics have been identified that are resistant to these enzymes.

Accordingly, what is needed is a process and system for high-throughput screening and identification of new antimicrobial drugs and compounds, including, but not limited to, antimicrobial peptides.

SUMMARY OF THE INVENTION

In various exemplary embodiments, the present invention comprises a solid supported branched linker assay system, comprising: an alpha compound and a beta compounds reversibly tethered to a solid support; a branched linker coupled to the solid support that tethers the alpha and beta compounds to the solid support; the branched linker comprising two cleavable linkers that are chemically distinct from one another, wherein a first chemically distinct linker tethers the β compound to the branched linker and a second chemically distinct linker tethers the α compound to the branched linker; and at least two means for cleaving the chemically distinct linkers, wherein a first cleavage means is configured to selectively cleave a first chemically distinct linker and a second cleavage means is configured to selectively cleave a second chemically distinct linker.

The branched linker is a C-terminal linker system that is synthesized onto the solid support and may comprise any number of carbons.

In embodiments, the solid support structure is two dimensional or three dimensional. Two dimensional embodiments may include but are not limited to slides, chips, plates, or any other two dimensional solid support structure commonly used in the art. Three dimension solid support structures may include, but are not limited to molecular beads, microspheres, magnetic micro-spheres, test tubes, petri dishes, microcentrifuge tubes, 96 well places, or any other three dimensional solid support structure commonly used in the art. The solid support may be comprised of but not limited to silicon, glass, polystyrene, latex, or any other materials commonly used as solid support structures. Further, the solid support may be comprised of any suitable two dimensional or three dimensional structure comprising a metal oxide coating. The solid support structure may be chemically modified to facilitate attachment of the linker system. Such modification may include but are not limited to treating the surface of the support structure with amino silane or epoxy silane, mercaptosilanization, derivatization of the surface with aminophenyl or aminopropyl, or coating the surface with isothiocyanate. In embodiments, the solid support is a polyethylene-grafted polystyrene bead.

The alpha or beta compounds utilized in the solid supported branched linker assay system may be small molecules, peptides, DNA/RNA aptamers, or antimicrobial peptides. In embodiments, the alpha or beta compounds are peptoids. The alpha or beta compounds may be directly or indirectly tethered to the solid support structure. In embodiments, the alpha and beta compounds are substantially identical.

Numerous linker systems may be appropriate for use in the present system. In embodiments, the first chemically distinct linker comprises a disulfide; and the first cleavage means comprises a reducing agent. The reducing agent employed may be any commercially available reducing agent. In embodiments, the reducing agent is dithiothreitol, β-mercaptoethanol, or tris-(2-carboxyethyl)phosphine. In one embodiment, the reducing agent is tris-(2-carboxyethyl)phosphine. Appropriate concentrations of the reducing agent may be from about 1 to about 100 mM. In alternate embodiments, the appropriate concentration of reducing agent may be up to about 50 mM. In still other embodiments, the concentration of reducing agent may be up to about 25 mM. Alternatively, the concentration of reducing agent may be between about 2 to about 14 mM. In one embodiment, the concentration of reducing agent is about 14 mM.

In other embodiments, the second cleavable linker comprises a methionine and the second cleavage means comprises cyanogen bromide.

The solid supported branched linker assay system may further comprise a means for screening the therapeutic effectiveness of of the beta compound and identifying the alpha compound. In non-limiting embodiments, the means for screening comprises: a growth media that has been inoculated with cells of interest; the growth media further comprising the alpha and beta compounds immobilized onto the solid support and the first cleavage means, forming a growth media complex; an incubation period during which the microorganism grows within and on the growth media complex and the first chemically distinct linker is cleaved, thereby removing the beta compound from the support structure; an assessment period during which therapeutic effectiveness of the beta compound is assessed within the growth media complex; a removal period, wherein the solid support and the alpha compound tethered thereto are removed from the growth media complex; a cleavage period wherein the second cleavage means selectively cleaves the second chemically distinct linker to release the alpha compound from the support media; a means for identifying the alpha compound; and an identification period, wherein the alpha compound is identified.

In embodiments, the growth media utilized is soft agar. However, embodiments can be envisioned with little or no agar.

The cells of interest that are inoculated within the growth media may be microorganisms such as bacteria or other prokaryotic cells. Alternatively, the cells of interest may be mammalian or other eukaryotic cells.

The assessment period discussed above may comprise an analysis of the amount of cell growth inhibition that surrounds the solid support after.

In one aspect of the invention mass spectrometry is the means for identifying at the alpha compound. Nuclear magnetic resonance spectroscopy may also be used to identify the structure of the compound.

A method is also disclosed in accordance with various embodiments of the present general inventive concept for identifying the effectiveness of therapeutic compounds. The method comprises reversibly coupling an alpha and a beta compound to a solid support through a branched linker, wherein the branched linker comprises at least two cleavable linkers that are chemically distinct from one another; the two cleavable linkers further comprising a first chemically distinct linker that tethers the beta compound to the branched linker and a second chemically distinct linker that tethers the alpha compound to the branched linker; and providing at least two means for cleaving the chemically distinct linkers, wherein a first cleavage means is configured to selectively cleave a first chemically distinct linker and a second cleavage means is configured to selectively cleave a second chemically distinct linker.

The method additionally includes screening for the therapeutic effectiveness of beta compound and identifying the alpha compound. In embodiments, to accomplish the screening process, a growth media is first inoculated with a microorganism of interest. In some embodiments, the growth media may be agar. As stated above, alternate types of growth media may also be appropriate for the method.

Next, the alpha and beta compounds tethered to the solid support and the first cleavage means are added to the growth media, forming a growth media complex. The method further comprises incubating the growth media complex, during which the microorganism grows within and on the growth media and the first chemically distinct linker is cleaved. The cleavage removes the beta compound from the support structure. When removed from the support structure, the beta compound is free to interact with the microorganism that is disposed in and around the support structure within the growth media complex.

The method additionally provides for assessing the therapeutic effectiveness of the cleaved compound within the growth media complex. This assessment may be performed by analyzing the amount of cells grown inhibition that surrounds the solid support, wherein a halo of inhibited cell growth is associated with a therapeutically effective compound. This halo of inhibited cell growth can be referred to as the zone of inhibition.

Upon finding a therapeutically effective compound, the method further includes removing the solid support and alpha compound tethered thereto from the growth media complex. Next, the embodiments of the method include adding the second cleavage means to the solid support and alpha compound tethered thereto to cleave the second chemically distinct linker. This releases the alpha compound from the support media. The final step of the method may comprise identifying the therapeutically effective compound. The identification may be performed by obtaining the structure of the alpha compound. In embodiments, the structure of the compound may be obtained through mass spectrometry. In alternate embodiments, the structure may be obtained through nuclear magnetic resonance spectroscopy.

In various exemplary embodiments, the present invention comprises a solid supported branched linker system and plate based high-throughput screening method for the identification of therapeutic compounds. Two or more compounds are immobilized or tethered onto the solid support through a branched linker that contains the two or more compounds. The linkers tethering the two or more compounds can be chemically manipulated individually. In embodiments, one compound is attached to the linker by a disulfide, which can be cleaved with reducing reagent during high-throughput screening to release the compound from the solid support to interact with the cells of interest. After identifying which solid supports contain effective therapeutic compound against the cells of interest, the solid support can be removed from the screening plate and the second compound cleaved off the solid support using cyanogen bromide. This second compound can then be analyzed by mass spectrometry or nuclear magnetic resonance to identify the structure of the effective therapeutic compound. High-throughput screening of the compound library is achieved by embedding the solid supported compound library into solid agar media inoculated with the cells or microorganism of interest and containing a small amount of reducing reagent to cleave one linker and release at least one compound attached to the branched linker system. As described above, effective therapeutic compounds will result in a zone of inhibition around the solid support, which can be removed and the second compound cleaved for compound identification.

In certain embodiments, the solid support used is Tenta-Gel®, which is a polyethylene grafted polystyrene. However, as stated above, any solid support may be used, including but not limited to polystyrene, latex beads, and any number of metal oxide supports. Embodiments of the branched linker system comprise two compounds; the first may be a disulfide that can be cleaved by a reducing reagent; the second may be a methionine that can be cleaved by cyanogen bromide. Embodiments and examples of the present invention described herein detail the use of peptoids immobilized on the branched linker system for antimicrobial identification. As would be apparent to one having ordinary skill in the art, other potential therapeutic compounds could be appended to the branched linker system in alternate embodiments, including but not limited to small molecules, peptides, or DNA/RNA aptamers.

In several nonlimiting embodiments, the invention comprises a Peptoid Library Agar Diffusion (PLAD) assay, which takes advantage of a solid-phase combinatorially produced library of peptoids on a chemically cleavable linker that can be screened within solid agar plates to readily identify potent antimicrobial peptoids against microbes of interest.

Embodiments of the screening process described herein utilize solid supported compounds embedded into lysogeny broth agar. Other potential solidified growth media could be used in alternate embodiments of this screening assay, including but not limited to Matrigel®, a gelatinous media that is secreted by Engelbreth-Holm-Swarm mouse sarcoma cells. Use of media such as Matrigel® is preferred in embodiments wherein the cells of interest to be inoculated within the growth media are mammalian cells. Other suitable solid support growth matrices will be apparent to those having skill in the art.

Other objects and advantages of this invention will become readily apparent from the ensuing description.

BRIEF DESCRIPTION OF THE FIGURES

FIG. 10A shows amines incorporated into a low diversity, proof-of-concept library on the PLAD linker.

FIG. 10B shows the average zones of inhibition for the antimicrobial peptoids identified from screening the proof-of-concept library.

FIG. 10C is a table showing the minimum inhibitory concentration (MIC) values for peptoid K15 tested against the ESKAPE pathogens.

FIG. 13 shows the amines incorporated into a low diversity, proof-of-concept library on the PLAD linker of FIG. 10A and the associated polyethylene-grafted polystyrene bead.

FIG. 20 is a table showing the identity, sequence, and molecular weight of each compound in the proof-of-concept library.

FIG. 24 is a table showing the identity and sequences of proof-of-concept peptoid library hits against *E. coli* ATCC 25922.

FIG. 25A shows the general structure of the proof-of-concept PLAD linked library.

FIG. 25B shows amine submonomers incorporated into each of the positions in the library.

FIG. 25C is a homology chart from hits identified from screening of the proof-of-concept library indicating the prevalence of each submonomer at each position.

DETAILED DESCRIPTION OF THE INVENTION

Abbreviations and Definitions

Figure 1:
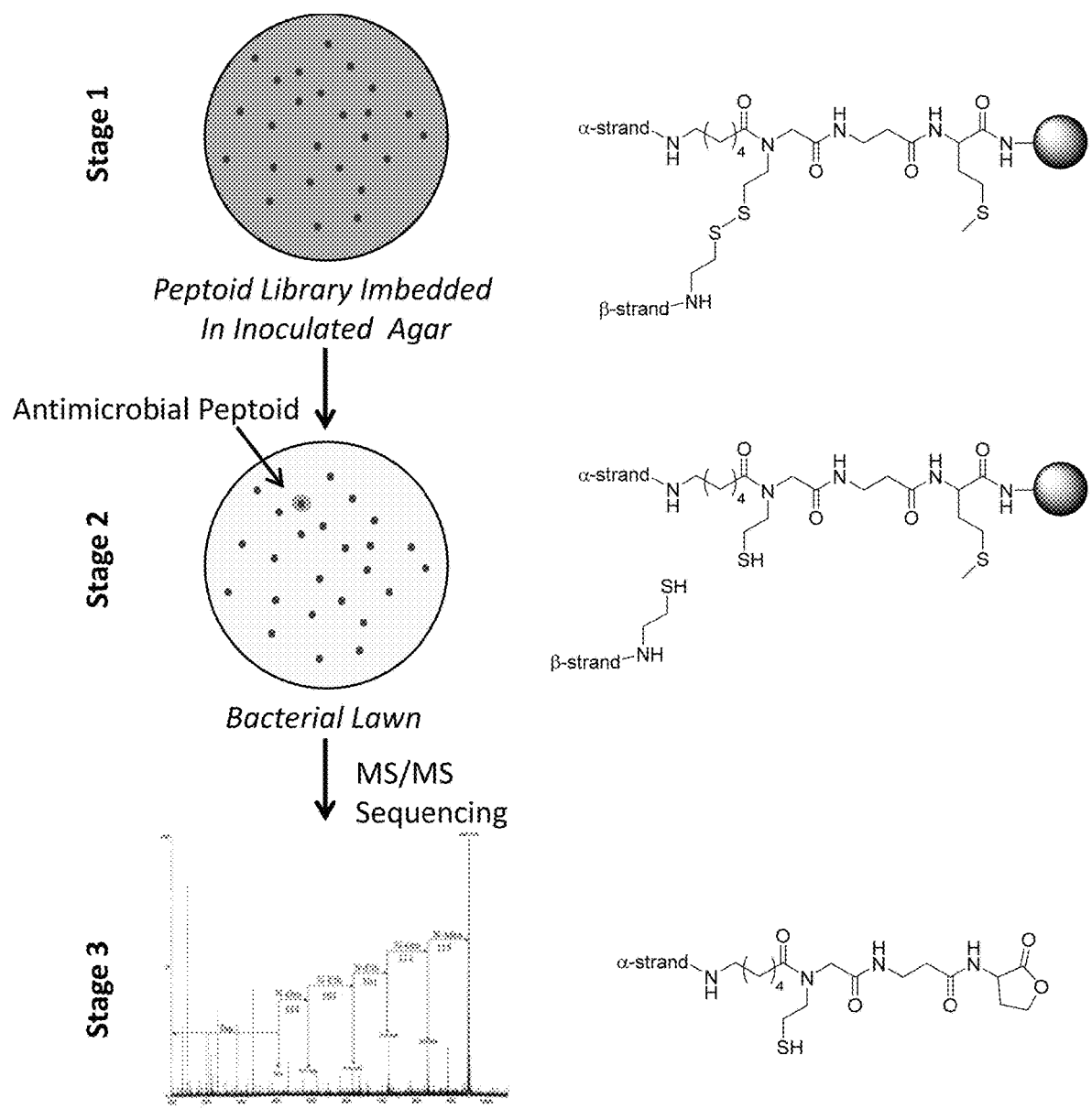
FIG. 1 shows a general PLAD Assay screening schematic. (Stage 1) Solid support compound library is embedded into soft agar that is inoculated with the microorganism of interest and contains a small amount of reducing reagent. (Stage 2) During incubation, the reducing reagent cleaves the disulfide bond, releasing the β-compound from the bead. A bacterial lawn forms with zones of inhibition forming around beads that release effective antimicrobial compounds. (Stage 3) Beads exhibiting zones of inhibition are removed from the plate and the α compound cleaved for analysis to determine the peptoid structure.

Detailed descriptions of one or more preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

The singular forms "a," "an," and "the" include plural reference unless the context clearly dictates otherwise. The use of the word "a" or "an" when used in conjunction with the term "comprising" in the claims and/or the specification may mean "one," but it is also consistent with the meaning of "one or more," "at least one," and "one or more than one."

Wherever any of the phrases "for example," "such as," "including" and the like are used herein, the phrase "and without limitation" is understood to follow unless explicitly stated otherwise. Similarly "an example," "exemplary" and the like are understood to be nonlimiting.

The term "substantially" allows for deviations from the descriptor that do not negatively impact the intended purpose. Descriptive terms are understood to be modified by the term "substantially" even if the word "substantially" is not explicitly recited. Therefore, for example, the phrase "wherein the lever extends vertically" means "wherein the lever extends substantially vertically" so long as a precise vertical arrangement is not necessary for the lever to perform its function.

The terms "comprising" and "including" and "having" and "involving" (and similarly "comprises", "includes," "has," and "involves") and the like are used unterchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

Antimicrobial Peptides and Peptoids

One class of antimicrobial compounds that are not susceptible to drug resistance mechanism is antimicrobial peptides (AMPs). AMPs serve as a natural part of the host-defense innate immune system of several organisms. There is little known antibiotic resistance to AMPs, likely due to their non-specific mode of killing. It is believed that most AMPs cause membrane permeabilization, resulting in leakage of cytoplasmic components and cell death. Other evidence indicates that some AMPs may bind to and disrupt DNA or RNA, which is not surprising given the amphipathic structure of these compounds. Although promising, AMPs have not been developed into legitimate therapeutics due to the poor proteolytic stability and low bioavailability of peptides. Several mimics of AMPs have been developed with the goal of preserving their advantages while circumventing their shortcomings. The most promising of these have been based on N-substituted glycines (termed peptoids) which are similar to peptides, but with the side chain shifted from the alpha-carbon to the amide-nitrogen. Peptoids are similar to peptides in function, yet they are not recognized by proteases and hence have a prolonged lifetime in vivo and improved bioavailability, making them excellent candidates as therapeutics.

The development of antimicrobial peptoids has relied on the mimicry of known AMPs and the generation of small (<20 compound) subsets of peptoids. This work has generated antimicrobial peptoids that are effective against *M. tuberculosis* and *P. aeruginosa* biofilms. The rapid development of MDR bacterial strains demands novel antibiotics and the above mentioned efficacy of peptoids demonstrates their potential as therapeutics. The need now is to develop methods to screen very large libraries of peptoid compounds against any bacteria of interest in a rapid fashion, thereby identifying antimicrobial peptoids that can treat new strains of MDR bacteria. Combinatorial libraries, generated by split-and-pool synthesis, are a way to generate large cohorts of potential therapeutic compounds in a relatively short period of time. These libraries are typically synthesized on the solid-phase to provide easy manipulation during synthesis and subsequent screening.

Problems with Identification of Antimicrobial Agents

Traditionally, the greatest source of new antimicrobial agents has been from natural products isolated from plants, bacteria, and other organisms. Though useful in the mid-1900s, identification of antimicrobial natural products has slowed substantially due to increased antimicrobial resistance and decreased sources of new natural products.

Detailed Description of Selected Exemplary Embodiments

In various exemplary embodiments, the invention comprises a molecular branched linker system immobilized on a solid support which displays parallel compounds of potential antimicrobial compounds. The linkers tethering the two parallel compounds can be chemically manipulated individually to allow for one compound to be released from the solid support during high-throughput screening, while maintaining the second compound on the solid support to be removed later for analysis to determine the compound structure. Thus, one of the two identical compounds is utilized for potency and assessment of therapeutic assessment, while the second compound may be utilized for structure deconvolution after screening. The invention also comprises the high-throughput assay, which entails embedding the solid-supported branch-linked potential antimicrobial compounds into agar in a Petri dish inoculated with the microorganism of interest.

In several nonlimiting embodiments, the invention comprises a Peptoid Library Agar Diffusion (PLAD) assay, which takes advantage of a solid-phase combinatorially produced library of peptoids on a chemically cleavable linker that can be screened within solid agar plates to readily identify potent antimicrobial peptoids against microbes of interest. Embodiments of the assay rely on a unique branched system with a disulfide linker that can be chemically cleaved after embedding the library into the agar. In contrast to previous bead diffusion assays, which have used photolabile linkers, the disulfide linker allows for cleavage after the beads are embedded in the agar, negating the need for UV light irradiation optimization and reducing cross contamination that would arise from irradiating the beads in one large batch and then spreading them across the agar. As an additional advantage, disulfide provides a slow-release linker, which allows for release of the tethered compound of interest after being embedded into a growth media, and provides sufficient opportunity for the released compound to interact with the microorganism within the growth media. Also, since the beads in embodiments of the present invention are surrounded by agar instead of spread on top, the compounds have better contact with bacteria, creating zones of clearance that are easier to read.

A central element to the PLAD Assay of the present invention is a C-terminal linker system that results in at least two identical peptoid compounds that can be individually chemically manipulated. In embodiments when two compounds are utilized, a first compound is termed alpha and a second compound is termed beta.

In alternate embodiments, the α and β compounds may not be identical. In such embodiments, the β compound may be the potential therapeutic that is tethered to the solid support via the disulfide linker, while the α compound is α compound that encodes for the β compound. Merely by way example, in embodiments, the β compound may comprise a peptoid while the α compound may comprise RNA or DNA that encodes for the β peptoid. Such embodiments may exist in several possible iterations, wherein the compound tethered to the disulfide linker is the therapeutic compound and at least one other compound (termed alpha) encodes for the therapeutic.

During the assay, soft agar may be inoculated with the microorganism of interest before addition of compound beads and a small amount of reducing reagent. In embodiments, the soft agar mixture is then poured onto a hard agar Petri dish and allowed to solidify, resulting in an even distribution of compound beads embedded in inoculated soft agar (FIG. 1; Stage 1). Alternatively, the compounded beads may be spread on the top of the agar mixture after solidification. The plate may then be incubated overnight, which allows for the bacteria to grow into a lawn and also results in cleavage of the disulfide bond with reducing reagent, releasing the beta-compound peptoid from the bead (FIG. 1; Stage 2). Incubation times may vary with the type cell embedded within the growth media. For most cell types an incubation period from 2-72 hours is sufficient achieve adequate cellular growth. In some embodiments, the incubation period may be 48 hours. In other embodiments, the incubation period may be as short as 2 hours.

When investigating antimicrobial agents, a compound that is an effective antimicrobial agent kills the microorganism surrounding the bead from which it was released, generating an easily read zone of inhibition, wherein little or no microorganism growth is observed. A similar zone of inhibition is observed with effective therapeutics in embodiments wherein the cell of interest are mammalian cells.

The bead embedded within the zone of inhibition can then be removed from the plate manually and the alpha-compound peptoid cleaved off to analyze by mass spectrometry (MS) and MS/MS (FIG. 1; Stage 3). In embodiments, manual removal is achieved through the use of surgical tweezers.

Synthesis of the C-terminal linker for the PLAD Assay (FIG. 2) can be performed on TentaGel® resin, a solid support which consists of polyethylene glycol grafted onto a polystyrene matrix. This feature allows swelling in both organic solvents, for synthesis, and aqueous solutions, for screening. However, any commercially available solid support may be utilized.

The number of carbons within the branched linker that may vary. Factors that may influence the number of carbons in the branched linker include, but are not limited to the number of associated compounds, the type of associated compounds, the type of chemically distinct linkers, and the cleavage means utilized. Embodiments of the C-terminal linker comprise from 2-50 carbon atoms. Additional embodiments may comprise 10-30 carbon atoms, inclusive. Embodiments may comprise 15-20 carbon atoms, inclusive. The C-terminal linker may comprise 3, 4, 5, 6, 7, 8, 9, 10, 11, 12, 13, 14, 15, 16, 17, 18, 19, 20, 21, 22, 23, 24, 25, 26, 27, 28, 29, or 30 or more carbon atoms.

Figure 2:
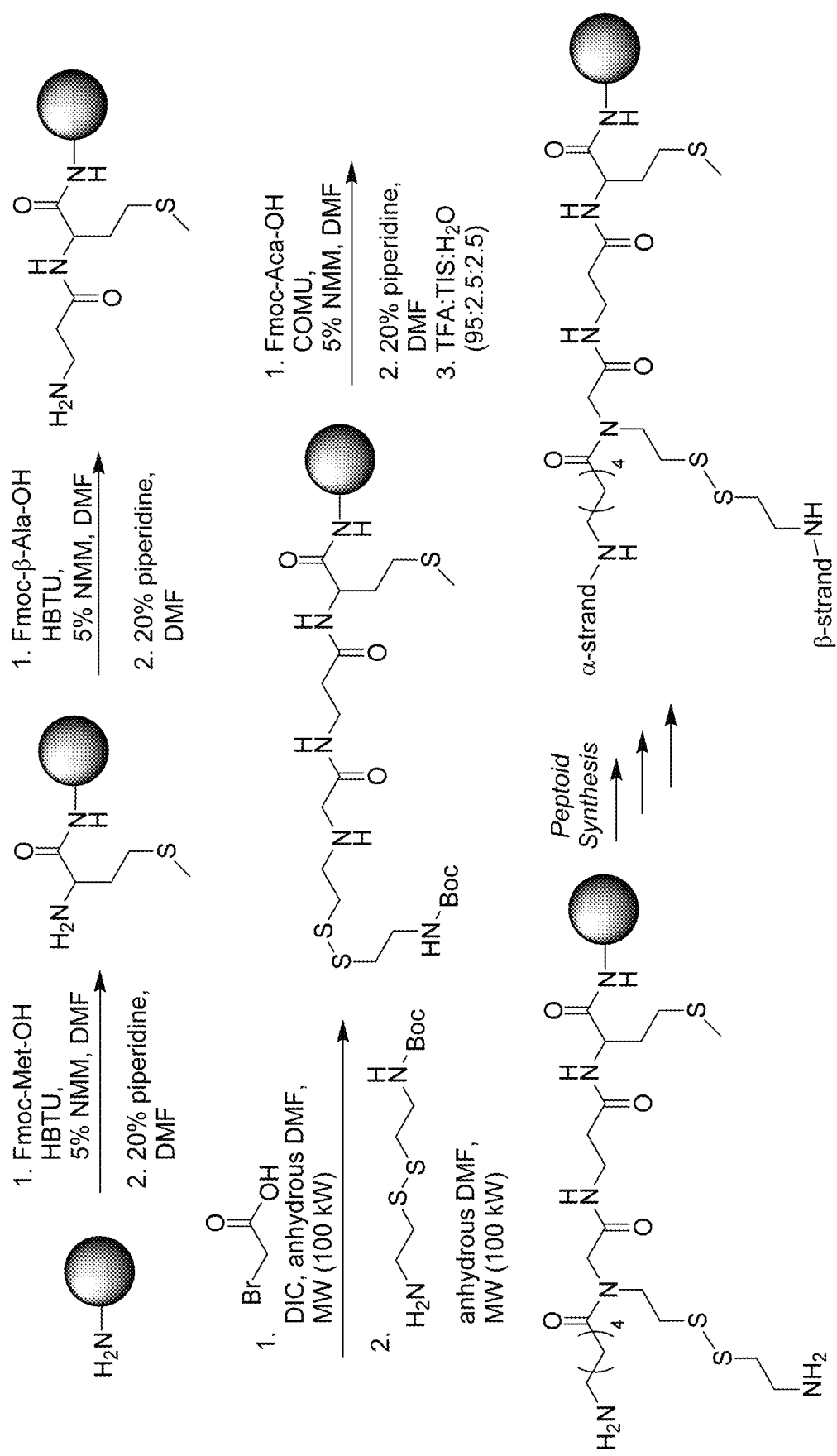
FIG. 2 shows the synthesis of branched PLAD Assay linker comprising two parallel compounds that can be chemically manipulated individually.

During synthesis in the FIG. 2 embodiment, the amino acid methionine is added first to the resin, which provides one way to orthogonally cleave the peptoid from the resin post-screening using cyanogen bromide, resulting in a homoserine lactone. Although methionine was utilized in the present embodiment, other methods of orthogonally cleaving the compound from the resin post-screening are also appropriate. One having skill in the art would recognize that any number of solid support chemical linkers that are commonly used in solid phase synthesis could be utilized in pace of methionine in alternate embodiments.

As shown in FIG. 2, after methionine addition, a spacer such as β-alanine was added to encourage movement of the rest of the linker system and peptoid away from the resin. Alternative spacers including, but are not limited to other amino acids, peptoid building blocks (such as aminohexanoic acid), or polymeric spacers (such as PEG).

In the s, the FIG. 2 embodiment, a sulfide linker can then be introduced via peptoid submonomer methods using bromoacetic acid followed by mono-Boc protected cystamine. In alternative embodiments, amino acids that contain the Boc-protected disulfide linker may be incorporated into this moiety to add the disulfide linker. In addition, the disulfide linker could be introduced by installing a cysteine followed by an oxidation reaction with another sulfur containing compound to form the disulfide. Additional methods of incorporating a disulfide linker will be apparent to those having skill in the art.

After adding the disulfide linker in FIG. 2, Fmoc-aminohexanoic acid was added to the N-terminus of the peptomer followed by removal of the Boc and Fmoc protecting groups. Alternative amine protecting groups may also be utilized. These alternative groups include, but are not limited to carboxybenzyl, tert-butyloxycarbonyl, trityl, N-1-(4,4-Dimethyl-2,6-dioxocyclohexylidene)ethyl. In this manner a linker system is produced with two free amino groups ready for peptoid synthesis to generate identical sequences with orthogonal chemical manipulation. Aminohexanoic acid, or any other suitable spacer may be utilized at the branch point in order to space out the two amino groups. Alternate spacers may include but are not limited amino acids (such as β-alanine), other peptoid building blocks, polymeric spacers (such as PEG), or small organic molecules. Without this spacer, cyclization of the two branches occurs during subsequent peptoid synthesis.

Figure 3:
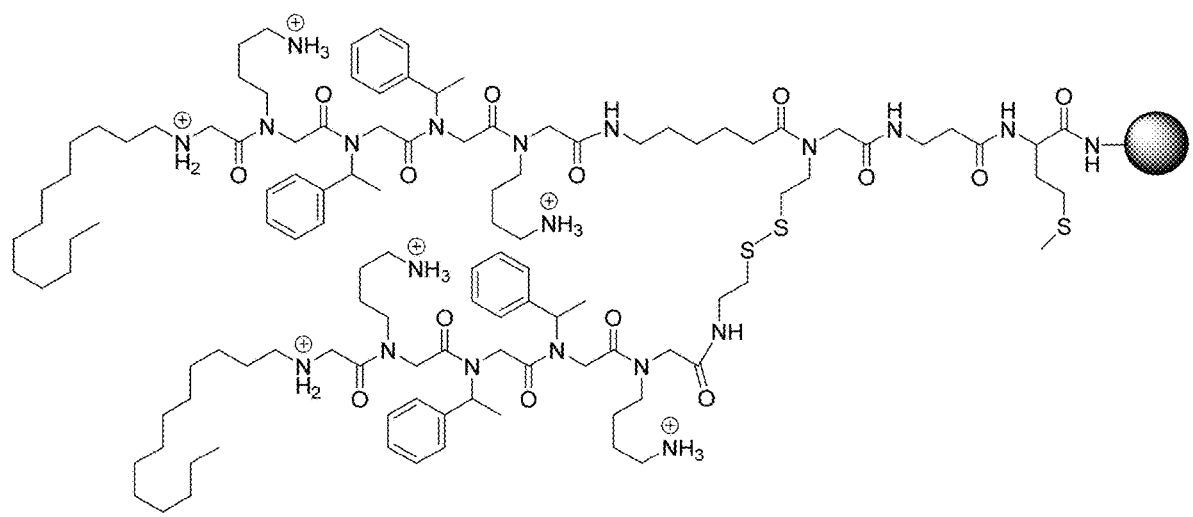
FIG. 3 shows a diagram of an antimicrobial peptoid ($C13_{4mer}$) synthesized onto the PLAD Assay linker.

After completion of the linker design, an antimicrobial peptoid or other potentially therapeutic compound may be added. As a proof of concept, a known antimicrobial peptoid was synthesized on the PLAD Assay linker for bacterial screening (FIG. 3). In the proof-of-concept embodiments, the peptoid of choice, termed C13$_{4mer}$, was designed by Barron et al., and involves the use of hydrophobic alkyl tails to mimic the antibacterial properties of lipopeptides. This addition of an alkyl tail allows the peptoid of interest to be shortened, while still retaining useful antimicrobial behavior. One benefit of the shortening involves limiting the number of reactions occurring in the peptoid process, allowing for a higher yield. Another benefit is the reduction in molecular weight of the compound when changing from a 10-15 submonomer length peptoid to a 3-5 submonomer length peptoid. The sequence of the C13$_{4mer}$ peptoid synthesized on the PLAD Assay linker was NTri-NLys-NPea-NPea-NLys. Nomenclature for peptoid submonomers uses standard three letter codes, as for amino acids, but prefixes the code with "N" to denote the placement of the side chain on the amide nitrogen. Synthesis was accomplished by peptoid submonomer methods using bromoacetic acid and mono-Boc-1,4-diaminobutane, phenylethylamine, and 1-tridecylamine. The acid sensitive Boc protecting group was used on 1,4-diaminobutane, as any unprotected NLys submonomers would act as branching points during bromoacylation. The Boc group was shown to still be attached after subsequent treatments with bromoacetic acid (data not shown) demonstrating its stability to weak acids and usefulness as a protecting group for this synthetic method. After final coupling of the tridecyl alkyl tail, the Boc groups were removed with triflouroacetic acid (TFA) and washed thoroughly to ensure residual acid was removed. As apparent to those skilled in the art, further compounds other than peptoids, may be tethered to the branched linker system without undue experimentation. Further compounds that may be tethered to the branched linker system of the present invention include, but are not limited to utilized in the solid supported branched linker assay system may be small molecules, peptides, DNA/RNA aptamers, or antimicrobial peptides.

Figure 4:
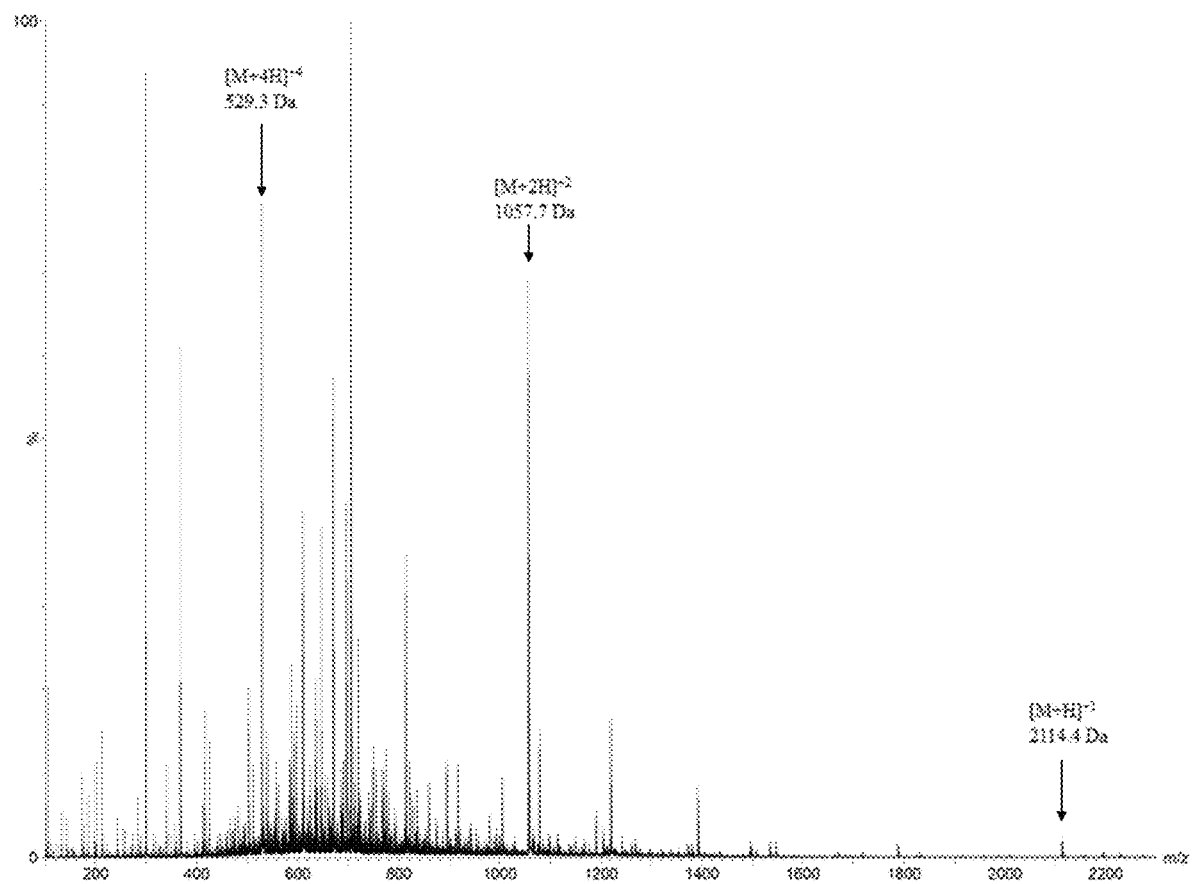
FIG. 4 shows the linear MS of the complete $C13_{4mer}$ compound.
Figure 5:
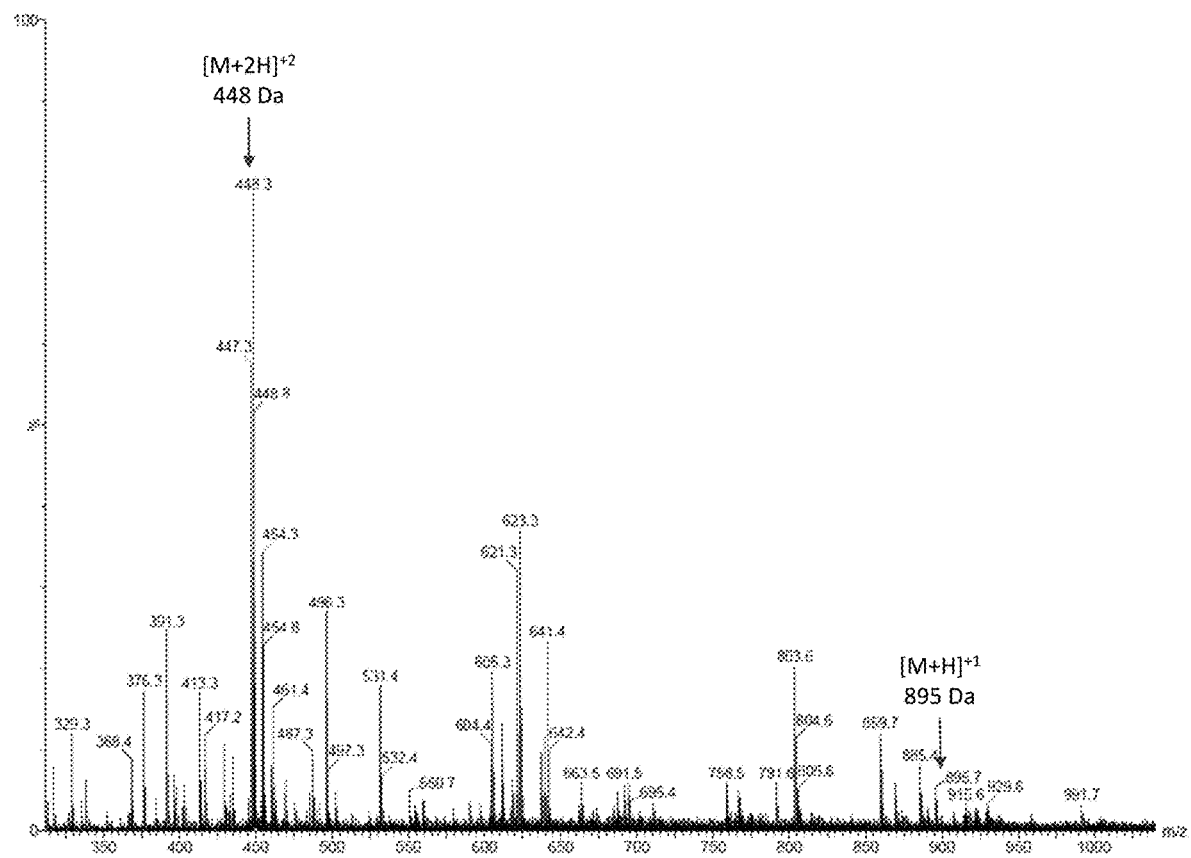
FIG. 5 shows the linear MS of $C13_{4mer}$ beta-strand compound.

For proof of concept, the synthesized C13$_{4mer}$ compound was analyzed by mass spectrometry (MS) to show the complete mass (FIG. 4) as well as tested to ensure that treatment with dithiothreitol (DTT), a reducing reagent, effectively cleaved the disulfide bond, yielding the beta compound (FIG. 5). This MS analysis confirms that the present invention enables chemical manipulation of the linkers tethering the two compounds individually.

Although both analyses were successful, the conditions of cyanogen bromide cleavage were optimized. In the present embodiment, conditions of cyanogen bromide cleavage were optimized in the presence of hydrochloric acid (HCl); however, as evident to one having skill in the art, alternate acids or concentrations of acids may be used to create a suitable environment for cyanogen bromide cleavage. In embodiments, after multiple cyanogen bromide cleavages were unsuccessful in 0.1 M HCl in water, the hydrophobicity of the cleavage solution was altered with addition of acetonitrile. After trying several different ratios, it was determined that an optimal ratio of 80:20 acetonitrile:water containing 0.1 M HCl resulted in the highest quality compound analysis by mass spectrometry. This could be in part due to the swelling properties of TentaGel® resin as well as a more non-polar solution helping the hydrophobic alkyl tails diffuse out of the bead and into solution. These data support full enablement and optimization for synthesis, chemical manipulation, and mass spectroscopic analysis of the PLAD Assay linker and the tethered compounds.

Enablement and optimization of the PLAD Assay screening conditions is discussed below. PLAD linked C13$_{4mer}$ was used to evaluate the most effective reducing reagent for the PLAD Assay against non-pathogenic *E. coli* (ATCC 25922); however, the disclosed methodology is applicable to a broad array of peptoids and other compounds. Further, the cells of interest are not required to be a non-pathogenic *E. Coli*. One having skill in the art could apply similar optimization of reducing agents for use with an array of prokaryotic or eukaryotic cells or other microorganisms.

Several common reducing reagents were examined at varying concentrations (0, 2, 6, 10, and 14 mM) to identify the most suitable reagent to effectively cleave the disulfide linker without significantly affecting microorganismal growth. The reagents tested were dithiothreitol (DTT), β-mercaptoethanol (BME), and tris-(2-carboxyethyl)phosphine (TCEP), but any commercially available reducing reagents may be suitable for use within the present invention. As would be understood by one having skill in the art, the optimal reducing agent and the concentration of the reducing agent may vary with the selection of the microorganism or other cell. In any case, the effectiveness at cleaving the disulfide linker and releasing the beta-compound peptoid may be evaluated by measuring the zone of inhibition, which may be defined as the area around the bead with no bacterial growth and measured from the edge of the bead to the start of bacterial lawn growth.

Figure 6:
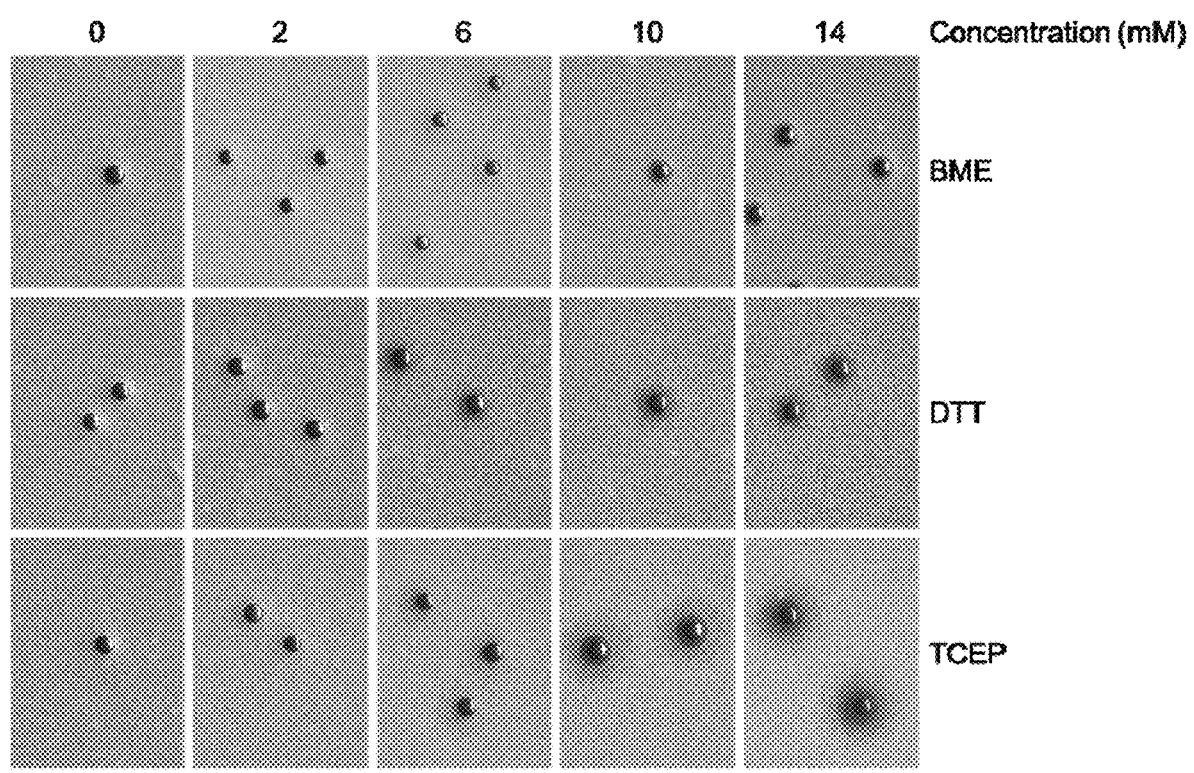
FIG. 6 shows images from a comparative PLAD Assay screening of three reducing agents tested at five different concentrations.
Figure 7:
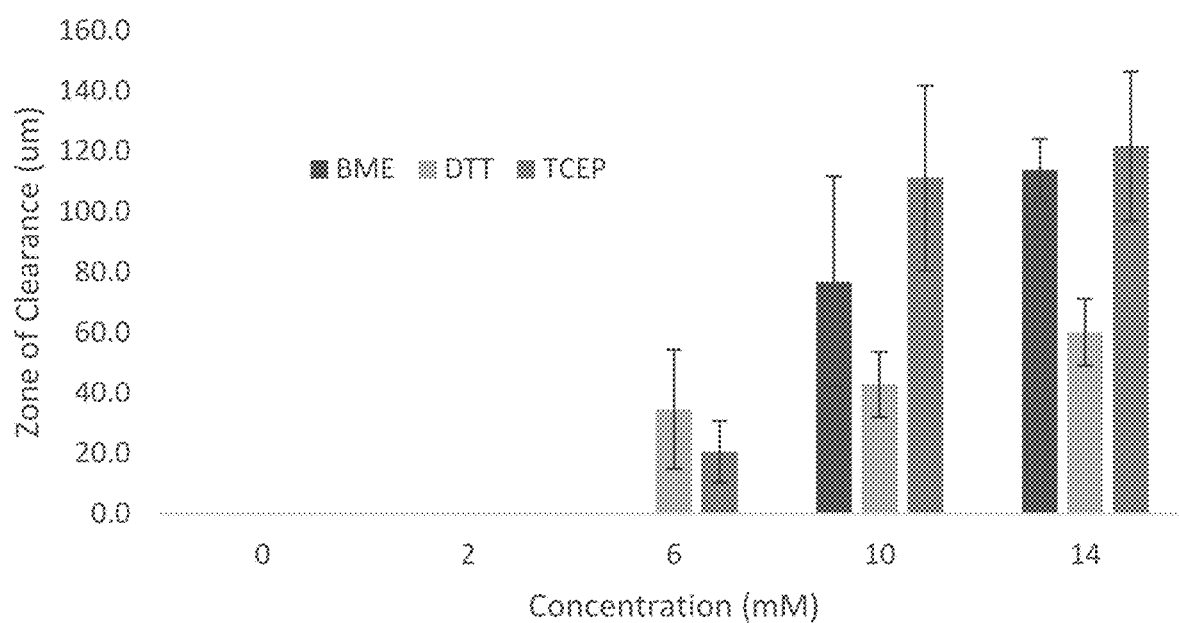
FIG. 7 is a graph of the zone of inhibition/clearance as a function of concentration for the three reducing agents of FIG. 6.
Figure 8:
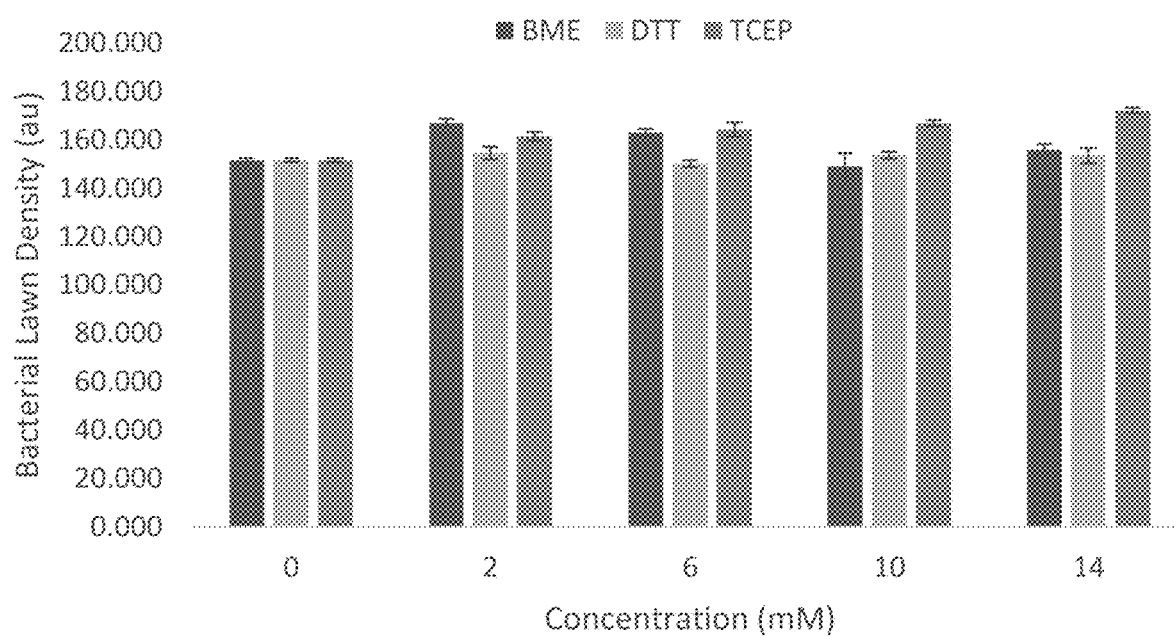
FIG. 8 is a graph of bacterial lawn density as a function of concentration for the three reducing agents of FIG. 6.
Figure 9A:
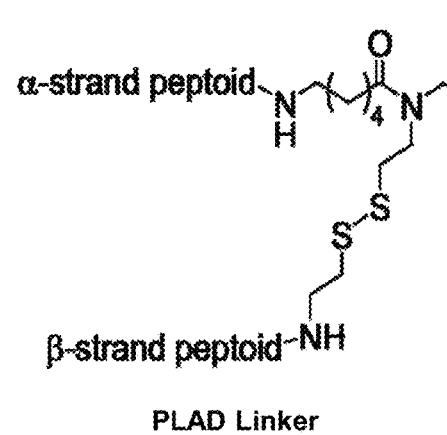
FIG. 9A shows the structure of the branched linker and solid support complex with two associated compounds. The α compound peptoid is tethered to the solid support via a methionine linker. The β compound peptoid is tethered to the solid support via a disulfide linker.
Figure 9B:
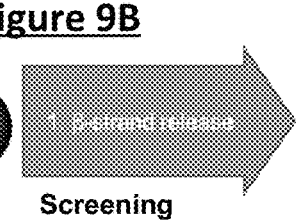
FIG. 9B shows a microscopic image showing the zone of inhibition surrounding the PLAD linker of FIG. 9A following cleavage and release of the β compound.
Figure 9C:
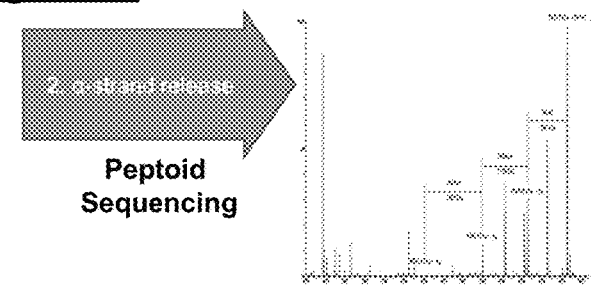
FIG. 9C shows the linear MS of the α compound following removal from grown media and subsequent cleavage from the PLAD linker of FIG. 9A.

In the proof-of-concept experiment, the effectiveness of reducing reagent on bacterial lawn growth was evaluated by measuring the luminosity of the light reflected by the bacterial lawn when illuminated from an angle, with denser bacterial lawns resulting in greater luminosity. All three reducing reagents resulted in concentration dependent zones of inhibition (FIG. 6 and FIG. 7). Comparatively, TCEP provided the clearest zones of inhibition, with the largest zones not surprisingly observed at 14 mM. Evaluation of the bacterial lawn density indicated that no significant effect on bacterial growth was observed for any of the reducing reagents at the concentrations tested (FIG. 8). Given this data, TCEP at a concentration of 14 mM was used for any subsequent PLAD Assays.

These data demonstrate the feasibility and utility of the branched linker system and the high-throughput PLAD Assay screening design. These methods are currently being applied to identify antimicrobial peptoids for proof-of-concept microorganisms, but can be applied to identify antimicrobial compounds of any sort against nearly any microorganism of interest.

Thus, it should be understood that the embodiments and examples described herein have been chosen and described in order to best illustrate the principles of the invention and its practical applications to thereby enable one of ordinary skill in the art to best utilize the invention in various embodiments and with various modifications as are suited for particular uses contemplated. Even though specific embodiments of this invention have been described, they are not to be taken as exhaustive. There are several variations that will be apparent to those skilled in the art.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1

Abstract

Rapid emergence of antimicrobial resistant organisms necessitates equally rapid methods for the development of new antimicrobial compounds. Of recent interest have been mimics of antimicrobial peptides known as antimicrobial peptoids, which exhibit similar potency to the former but with improved proteolytic stability. Presented herein is a high-throughput method to screen libraries of antimicrobial peptoids immobilized on beads embedded into solid media. Termed the peptoid library agar diffusion (PLAD) assay, this assay allows for individual chemical manipulation of two identical peptoid compounds. One compound can be released to diffuse out from a solid support bead and interact with the microorganism during screening. The other compound can be cleaved after screening from beads showing strong antimicrobial activity and analyzed by mass spectrometry to deconvolute the structure of the peptoid. This method was applied to a small library of peptoids to identify an antimicrobial peptoid with modest efficacy against the ESKAPE pathogens.

Keywords: peptoids, high-throughput, antimicrobial, combinatorial library

The increasing prevalence of multidrug-resistant (MDR) bacterial infections in the clinic necessitates methods to rapidly identify potent new antimicrobial agents that are effective against MDR bacteria. Antimicrobial resistance (AMR) is considered by the World Health Organization to be a major threat to global public health, resulting in a significant rise in global mortality rates and a significant decline in economic growth due to the growing cost of bacterial infection treatment.[1] A recent study predicted that by the year 2050, AMR will result in 10 million premature deaths per year worldwide and roughly $100 trillion USD in lost economic output.[2] Bacterial resistance is a growing problem due to increasing and improper use of antibiotics combined with the ability of bacteria to readily transmit information from one microbe to another.[3,4] Common mechanisms of bacterial resistance include drug efflux pumps and enzymes that break down common antibiotics, such as β-lactamases and aminoglycosides.[3,4] There is now a need for antimicrobial compounds that are not susceptible to these drug resistance mechanisms.

One such class that has drawn particular interest lately is antimicrobial peptides (AMPs). AMPs serve as a natural part of the host-defense innate immune system of several organisms.[5,6] There is little known antibiotic resistance to AMPs, likely due to their nonspecific mode of killing.[7] It is believed that most AMPs cause membrane permeabilization, resulting in leakage of cytoplasmic components and cell death.[5,7] Other evidence indicates that some AMPs may bind to and disrupt DNA or RNA, which is not surprising given the amphipathic structure of these compounds.[5,7] Although promising, AMPs have not been developed into legitimate therapeutics because of the poor proteolytic stability and low bioavailability of peptides.[8,9] Several mimics of AMPs have been developed with the goal of preserving their advantages while circumventing their shortcomings.[20] One promising class of these have been based on N-substituted glycines (termed peptoids) which are similar to peptides, but with the side chain shifted from the α-carbon to the amide-nitrogen.[9,11] Peptoids are similar to peptides in function, yet they are not recognized by proteases and hence have a prolonged lifetime in vivo as well as improved bioavailability, making them excellent candidates as therapeutics.9

The development of antimicrobial peptoids has relied on the mimicry of known AMPs and the generation of small (<20 compound) subsets of peptoids.12-17 This work has generated antimicrobial peptoids that are effective against *Mycobacterium tuberculosis* and *Pseudomonas aeruginosa* biofilms.13,14 The rapid development of MDR bacterial strains demands novel antibiotics, and the above-mentioned efficacy of peptoids demonstrates their potential as therapeutics. The need now is to develop methods to screen very large libraries of peptoid compounds against any bacteria of interest in a rapid fashion, thereby identifying antimicrobial peptoids that can treat new strains of MDR bacteria. Combinatorial libraries, generated by split-and-pool synthesis, are a way to generate large cohorts of potential therapeutic compounds in a relatively short period of time.18,19 Combinatorial libraries of peptoids, first synthesized by Zuckermann et al.,20 have been used to identify inhibitors of VEGFR21 and antibody ligands,22 among other applications. These libraries are typically synthesized on the solid-phase to provide easy manipulation during synthesis and subsequent screening.18 Combined with high-throughput screening methods, combinatorial libraries represent a powerful tool for drug discovery. The work detailed here introduces a peptoid library agar diffusion (PLAD) assay, which takes advantage of a solid-phase combinatorially produced library of peptoids on a chemically cleavable linker that can be screened within solid agar plates to readily identify potent antimicrobial peptoids against microbes of interest. This PLAD assay relies on a unique branched system with a disulfide linker that can be chemically cleaved after embedding the library into the agar. In contrast to previous bead diffusion assays, which have used photolabile linkers,23-25 the disulfide linker allows for cleavage after the beads are embedded in the agar, negating the need for irradiation optimization and reducing cross contamination that would arise from irradiating the beads in one large batch and then spreading them across the agar. Also, since the beads are surrounded by agar instead of spread on top, the compounds have better contact with bacteria, creating zones of inhibition that are easier to read.

The key to the PLAD Assay is a C-terminal linker system that results in two identical peptoid compounds, termed the alpha and beta compounds, that can be individually chemically manipulated. During the assay, soft agar is inoculated with the microorganism of interest before addition of compound beads and a small amount of reducing reagent. The soft agar mixture is then poured onto a hard agar Petri dish and allowed to solidify, resulting in an even distribution of compound beads embedded in inoculated soft agar (FIG. 1, stage 1). The plate is then incubated overnight, which allows for the bacteria to grow into a lawn and also results in cleavage of the disulfide bond with reducing reagent, releasing the beta-compound peptoid from the bead (FIG. 1, stage 2). A peptoid compound that is an effective antimicrobial agent kills the microorganism surrounding the bead it was released from, generating an easily read zone of inhibition. This bead can then be removed from the plate manually, and the alpha-compound peptoid cleaved to analyze by mass spectrometry (MS) and MS/MS (FIG. 1, stage 3).

Synthesis of the C-terminal linker in the PLAD Assay was done on TentaGel® resin, a solid support which consists of polyethylene glycol grafted onto a polystyrene matrix. This feature allows swelling in both organic solvents, for synthesis, and aqueous solutions, for screening. The amino acid methionine is added first to the resin (FIG. 2), which provides a way to orthogonally cleave the peptoid from the resin postscreening using cyanogen bromide. Resulting in a homoserine lactone, use of a methionine for orthogonal release of the compound from the resin is now common in combinatorial library synthesis and screening.26,27 After methionine, β-alanine is added as a spacer to help move the rest of the linker system and peptoid away from the resin. The disulfide linker is then introduced via peptoid submonomer methods11 using bromoacetic acid followed by mono-Boc protected cystamine. Lastly, Fmoc-aminohexanoic acid was added to the N-terminus of the peptomer followed by removal of the Boc and Fmoc protecting groups. This produces a linker system with two free amino groups ready for peptoid synthesis to generate identical sequences with orthogonal chemical manipulation. Aminohexanoic acid was chosen to use at the branch point in order to space out the two amino groups. Without this spacer, cyclization of the two branches was observed during subsequent peptoid synthesis (data not shown).

Figure 14:
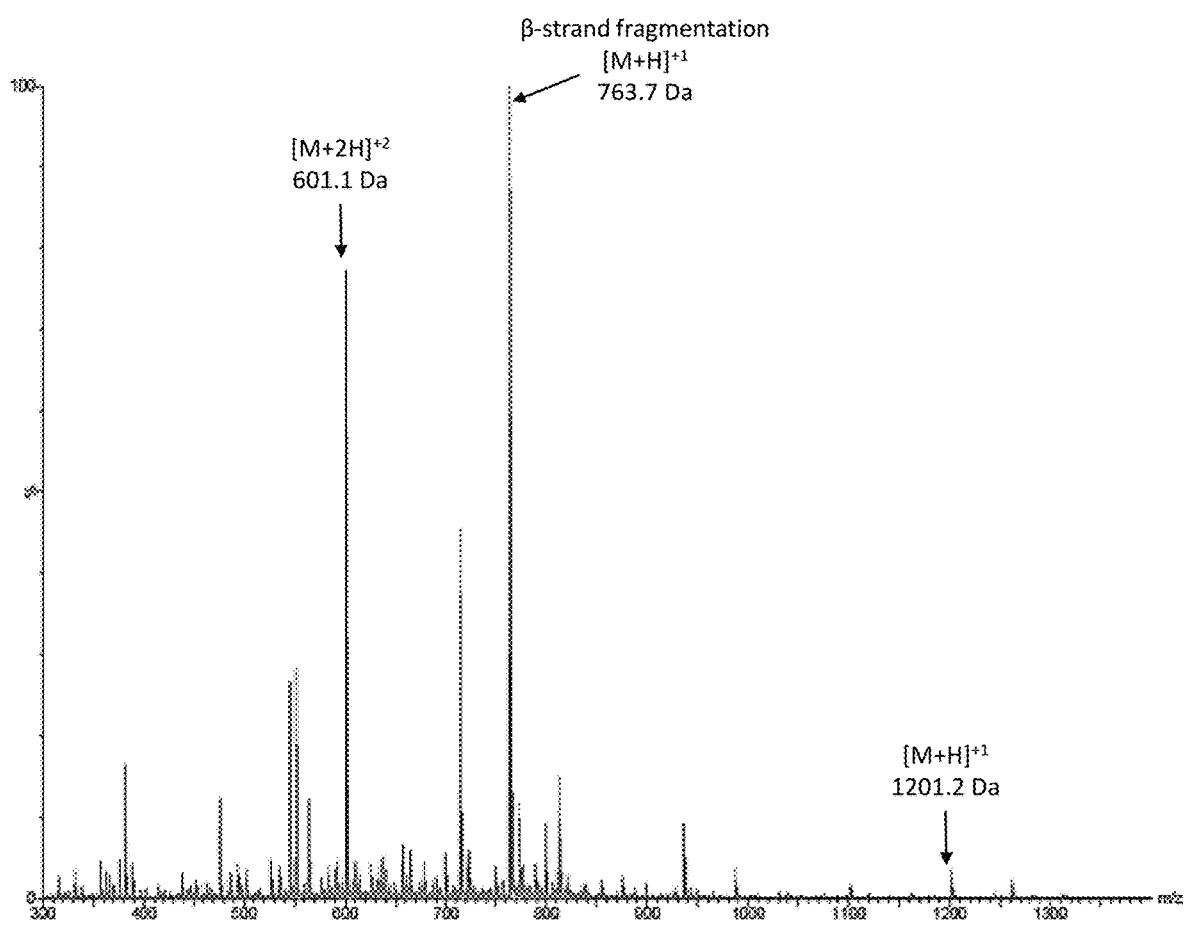
FIG. 14 is a linear MS of complete test peptoid, showing the desired compound at 1201.2 Da (M+H) and 601.1 Da (M+2H). The disulfide bond is easily fragmented during MS analysis, giving the complete compound minus the β-compound at 763.7 Da (M+H).
Figure 15:
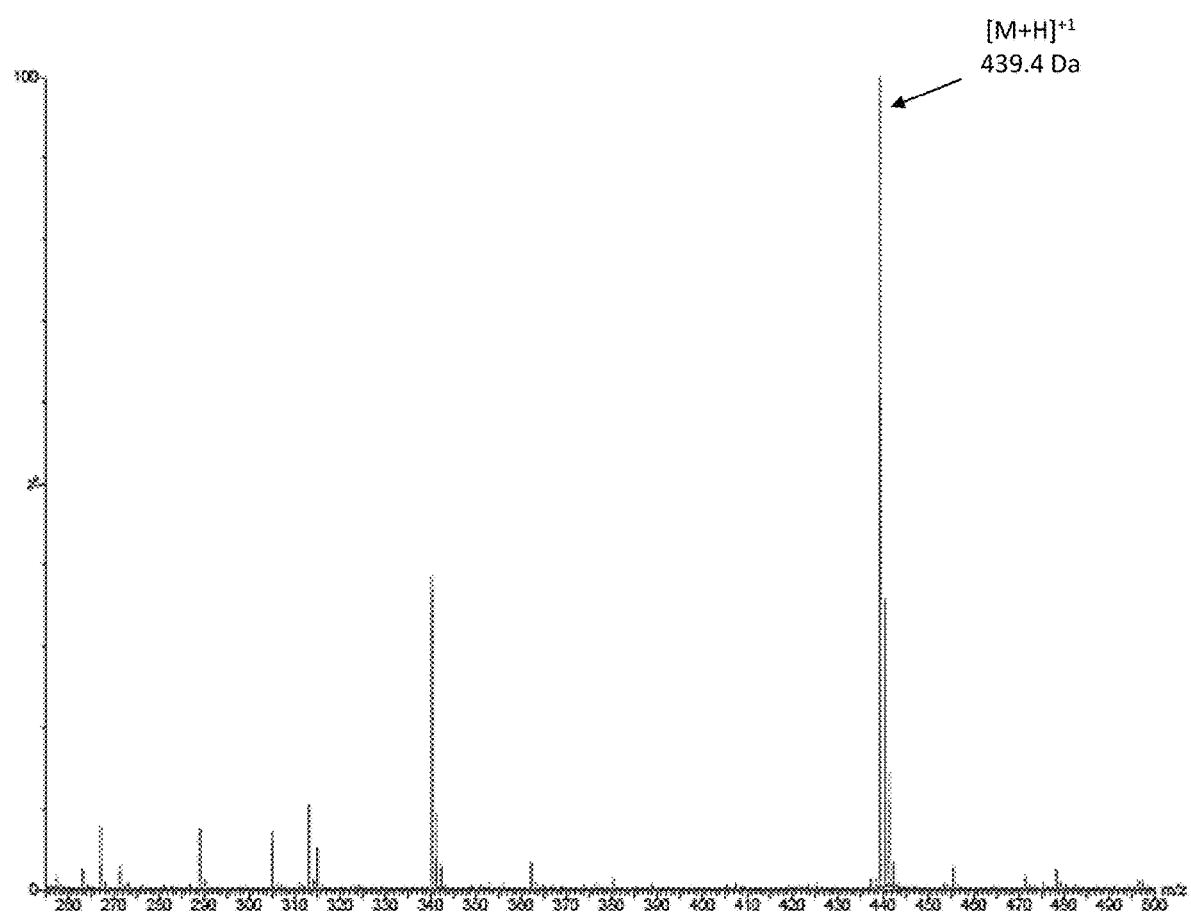
FIG. 15 is a linear MS of the β-compound of the test peptoid at 439.4 Da (M+H), released from the PLAD linker by treatment with TCEP.
Figure 16:
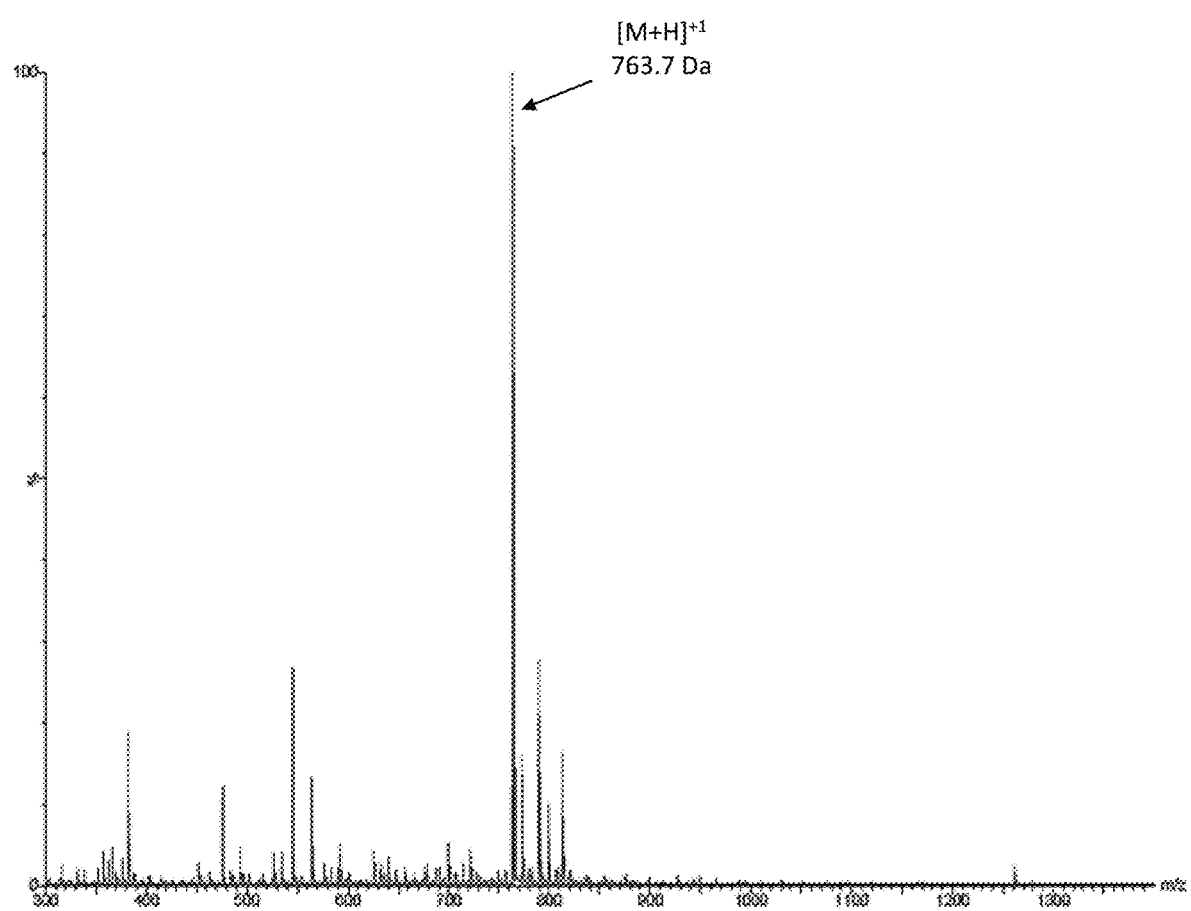
FIG. 16 is a linear MS of the α-compound of the test peptoid at 763.7 Da (M+H) after β-compound cleavage and release by TCEP.
Figure 17:
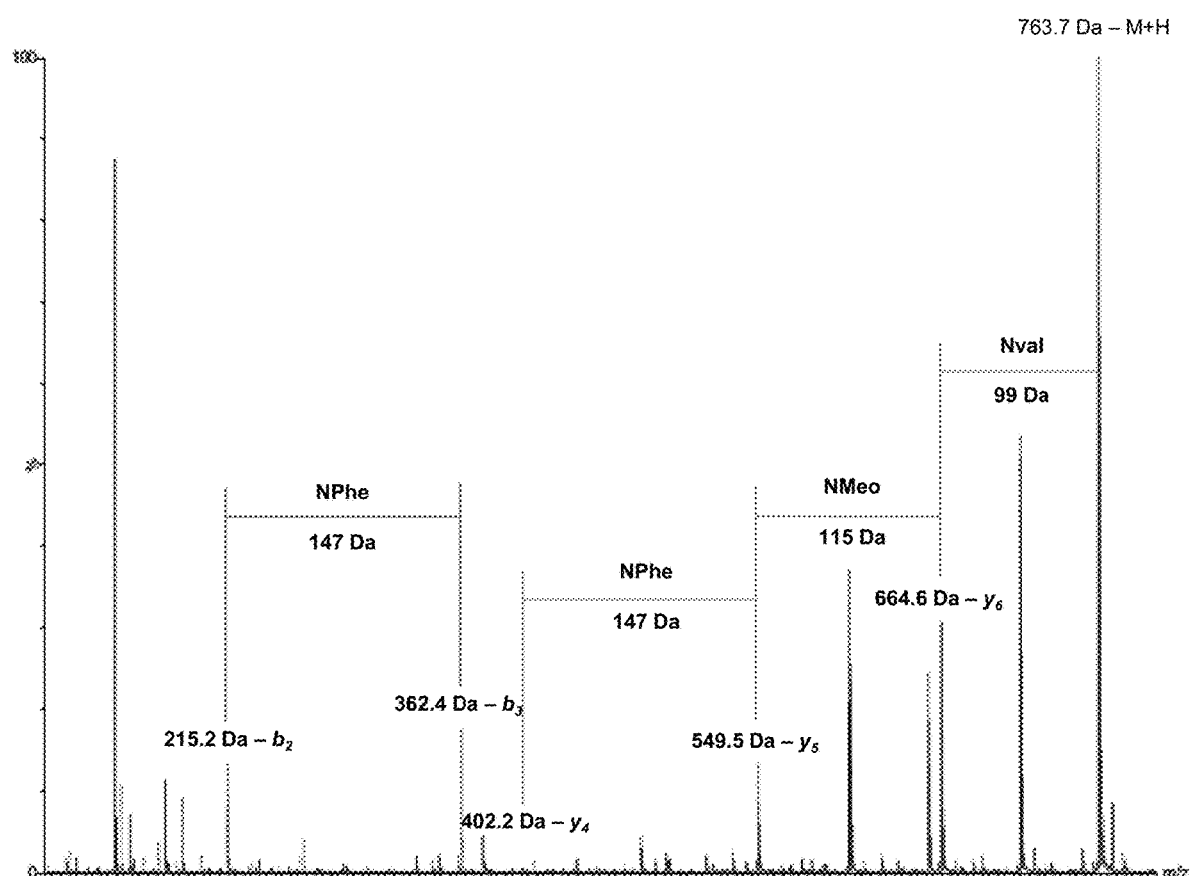
FIG. 17 is a tandem MS of the α-compound of the test peptoid after β-compound cleavage and release by TCEP. The sequence of this compound (NVal-NMeo-NPhe-PLAD linker) can be confirmed using both y ions and b ions.

Once the initial linker design was completed, a test peptoid was synthesized onto it to confirm the chemical manipulability of the PLAD linker. The submonomer sequence of the test peptoid was NVal-NMeo-NPhe. Nomenclature for peptoid submonomers uses standard three letter codes, as for amino acids, but prefixes the code with "N" to denote the placement of the side chain on the amide nitrogen. Synthesis was accomplished by peptoid submonomer methods11 using bromoacetic acid, diisopropylcarbodiimide, and the amines isopropylamine (NVal), 2-methoxyethylamine (NMeo), and benzyl amine (NPhe). The test peptoid was analyzed by mass spectrometry (MS) to show the complete mass (FIG. 14) as well as tested to ensure that treatment with tris(2-carboxyethyl)phosphine (TCEP), a reducing reagent, effectively cleaved the disulfide bond, yielding the β-compound peptoid (FIG. 15). Lastly, the remaining α-compound peptoid after TCEP treatment was cleaved from the resin with cyanogen bromide then analyzed by MS (FIG. 16) and MS/MS (FIG. 17). The resultant spectra confirmed the peptoid sequence and demonstrated the ability to deconvolute the sequence of a library peptoid after screening. Although all these analyses were successful, the conditions of cyanogen bromide cleavage had to be optimized. After multiple cyanogen bromide cleavages were unsuccessful for hydrophobic compounds in 0.1 M HCl in water, the hydrophobicity of the cleavage solution was altered with addition of acetonitrile. After trying several different ratios (data not shown), it was determined that an optimal ratio of 80:20 acetonitrile:water containing 0.1 M HCl resulted in the highest quality compound analysis by mass spectrometry. This could be in part due to the swelling properties of TentaGel® resin, as well as a more nonpolar solution aiding diffusion of the hydrophobic peptoid out of the bead and into solution.

Figure 18:
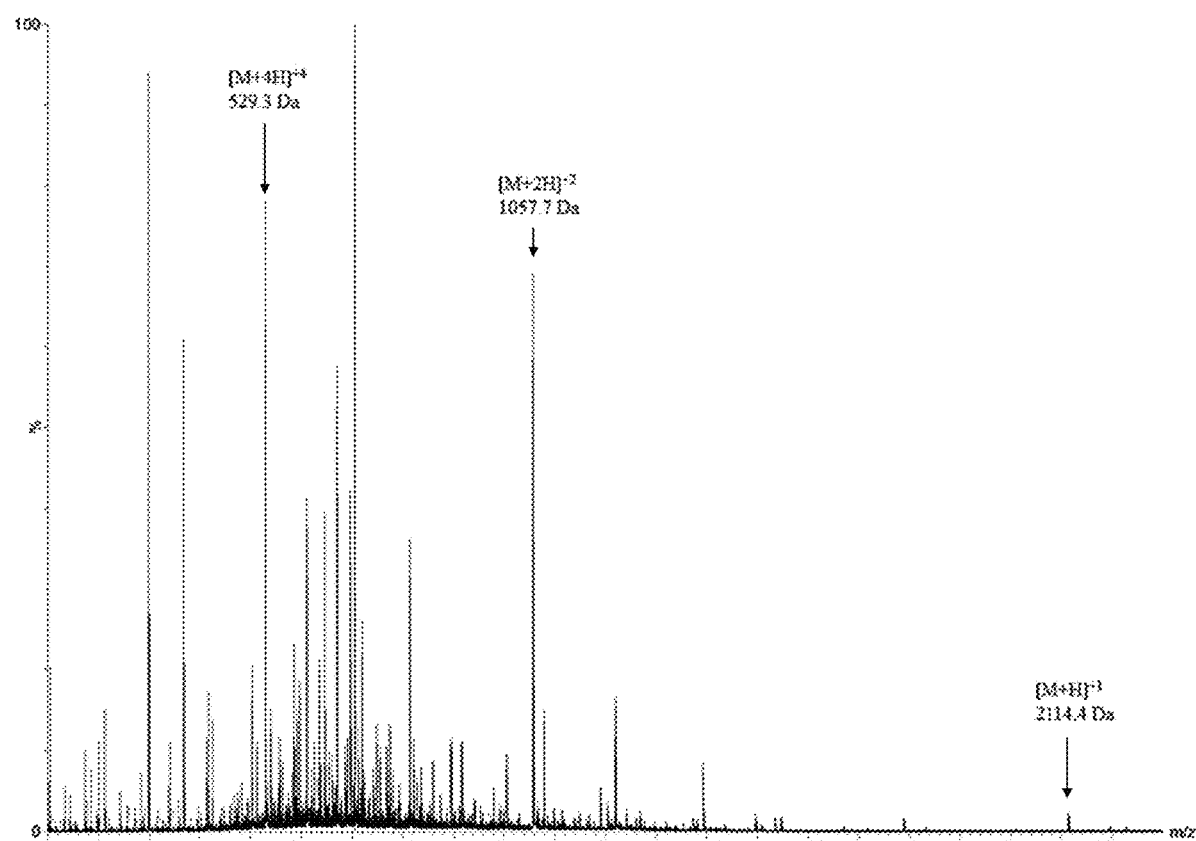
FIG. 18 is a linear MS of the complete $C13_{4mer}$, containing both the α and β-compounds of the peptoid.
Figure 19:
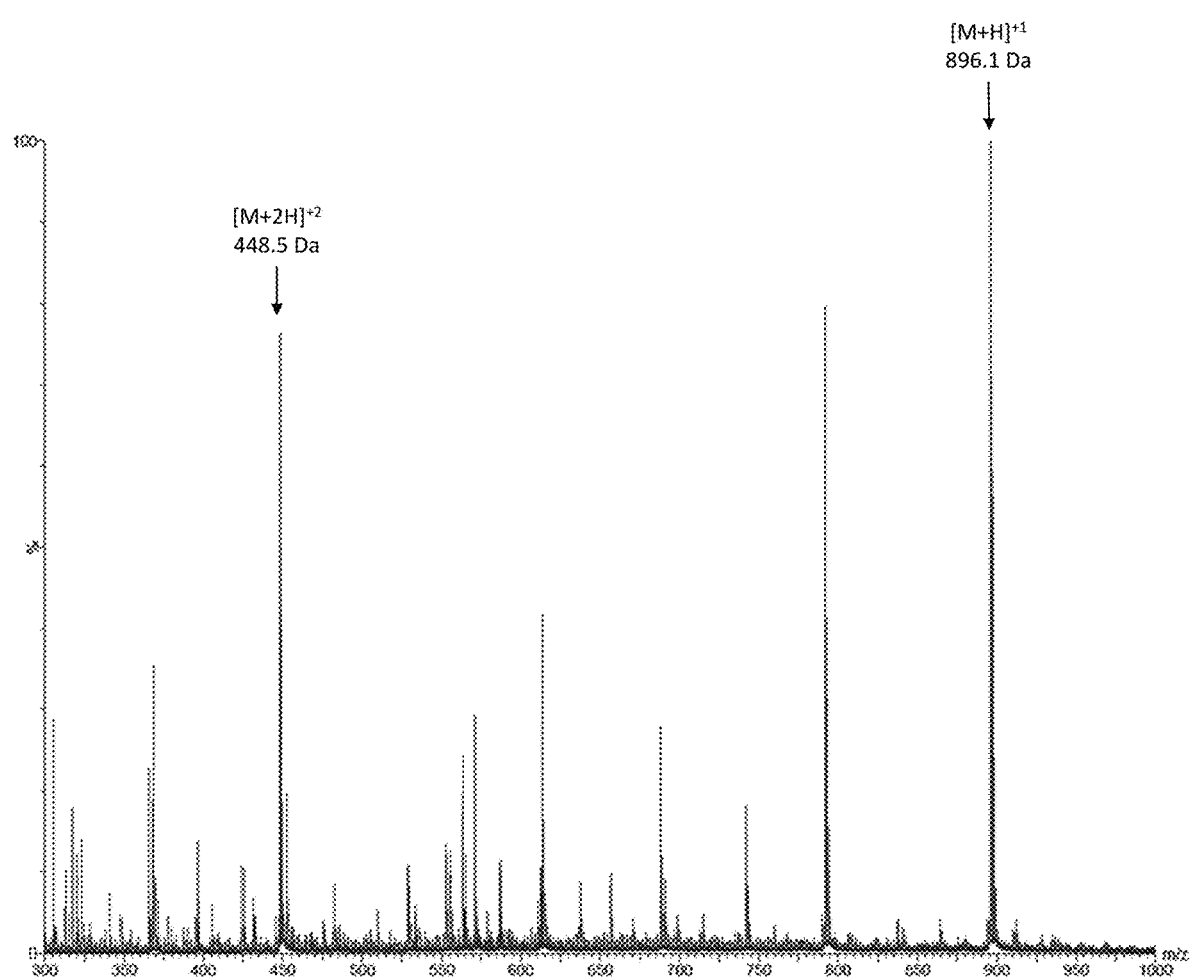
FIG. 19 is a linear MS of the β-compound of the PLAD linked $C13_{4mer}$, released using 1 mM TCEP.

With conditions optimized for synthesis, chemical manipulation, and mass spectroscopic analysis of the PLAD Assay linker and peptoid compounds, we next set out to optimize PLAD Assay screening conditions. A known antimicrobial peptoid was synthesized on the PLAD Assay linker as a proof-of-concept compound for bacterial screening (FIG. 3). The peptoid of choice, termed C134mer, was designed by Barron et al.13,14 and involves the use of hydrophobic alkyl tails to mimic the antibacterial properties of lipopeptides.28 The addition of an alkyl tail allows the peptoid of interest to be shortened, while still retaining useful antimicrobial behavior. As shown by Barron et al.,28 incorporation of 10 or 13 carbon alky tails onto pentameric antimicrobial peptoids yields similar potency to peptoids that are 12 to 16 submonomers in length but without long alkyl tails. One benefit of the shortening involves limiting the number of reactions occurring in the peptoid process, allowing for a higher yield. Another benefit is the reduction in molecular weight of the compound when changing from a 10-15 submonomer length peptoid (~1250 Da on average) to a 3-5 submonomer length peptoid (~400 Da on average). The sequence of the C134mer peptoid synthesized on the PLAD Assay linker was NTri-NLys-NPea-NPea-NLys. Synthesis was again accomplished by peptoid submonomer methods11 using bromoacetic acid, diisopropylcarbodiimide, and mono-Boc-1,4-diaminobutane (NLys), (±)-phenylethylamine (NPea), and 1-tridecylamine (NTri). The acid sensitive Boc protecting group was used on 1,4-diaminobutane, as any unprotected NLys submonomers would act as branching points during bromoacylation. The Boc group was shown to still be attached after subsequent treatments with bromoacetic acid (data not shown) demonstrating its stability to weak acids and usefulness as a protecting group for this synthetic method. After the final coupling of the tridecyl alkyl tail, the Boc groups were removed with trifluoroacetic acid (TFA) and the resin washed thoroughly to ensure residual acid was removed. The synthesized $C13_{4mer}$ compound was analyzed by mass spectrometry (MS) to show the complete mass (FIG. 18) as well as tested to ensure that treatment with TCEP effectively cleaved the disulfide bond, yielding the β-compound (FIG. 19).

PLAD linked $C13_{4mer}$ was subsequently used to evaluate the most effective reducing reagent for the PLAD assay (FIG. 1) against relatively nonpathogenic *Escherichia coli* (ATCC 25922). Several common reducing reagents were examined at varying concentrations (0, 2, 6, 10, and 14 mM) to identify the most suitable reagent to effectively cleave the disulfide linker without significantly affecting microorganismal growth. The reagents tested were dithiothreitol (DTT), β-mercaptoethanol (BME), and tris(2-carboxyethyl)phosphine (TCEP). Effectiveness at cleaving the disulfide linker and releasing the beta-compound peptoid was evaluated by measuring the zone of inhibition, defined as the area around the bead with no bacterial growth and measured from the edge of the bead to the start of bacterial lawn growth. Effect of reducing reagent on bacterial lawn growth was evaluated by measuring the luminosity of the light reflected by the bacterial lawn when illuminated from an angle, with denser bacterial lawns resulting in greater luminosity. All three reducing reagents resulted in concentration dependent zones of inhibition (FIGS. 6 and 7). Comparatively, TCEP provided the clearest zones of inhibition, with the largest zones not surprisingly observed at 14 mM. Evaluation of the bacterial lawn density indicated that no significant effect on bacterial growth was observed for any of the reducing reagents at the concentrations tested (FIG. 8). Given this data, TCEP at a concentration of 14 mM was used for any subsequent PLAD Assays.

To evaluate the usefulness of the PLAD Assay in identifying antimicrobial peptoids, a very small proof-of-concept library was synthesized on the PLAD linker using semicombinatorial chemistry (FIG. 10A). Three aromatic submonomers (furfurylamine, benzylamine, and 1-phenylethylamine) were randomly incorporated into the first C-terminal position of this library, two cationic submonomers (mono-Boc-diaminoethane and mono-Boc-diaminobutane) were randomly incorporated into the second position, and three hydrophobic submonomers (isopropylamine, 1-aminodecane, and 1-aminotridecane) were randomly incorporated into the third position. These submonomers were chosen for this proof-of-concept library because previous studies have shown that peptoids comprised of cationic and hydrophobic submonomers exhibit strong antimicrobial activity.[15,28,29] This produced a library with 18 unique peptoid sequences (FIG. 20) that could be screened to demonstrate the utility of the PLAD Assay and identify a novel antimicrobial agent.

Figure 21:
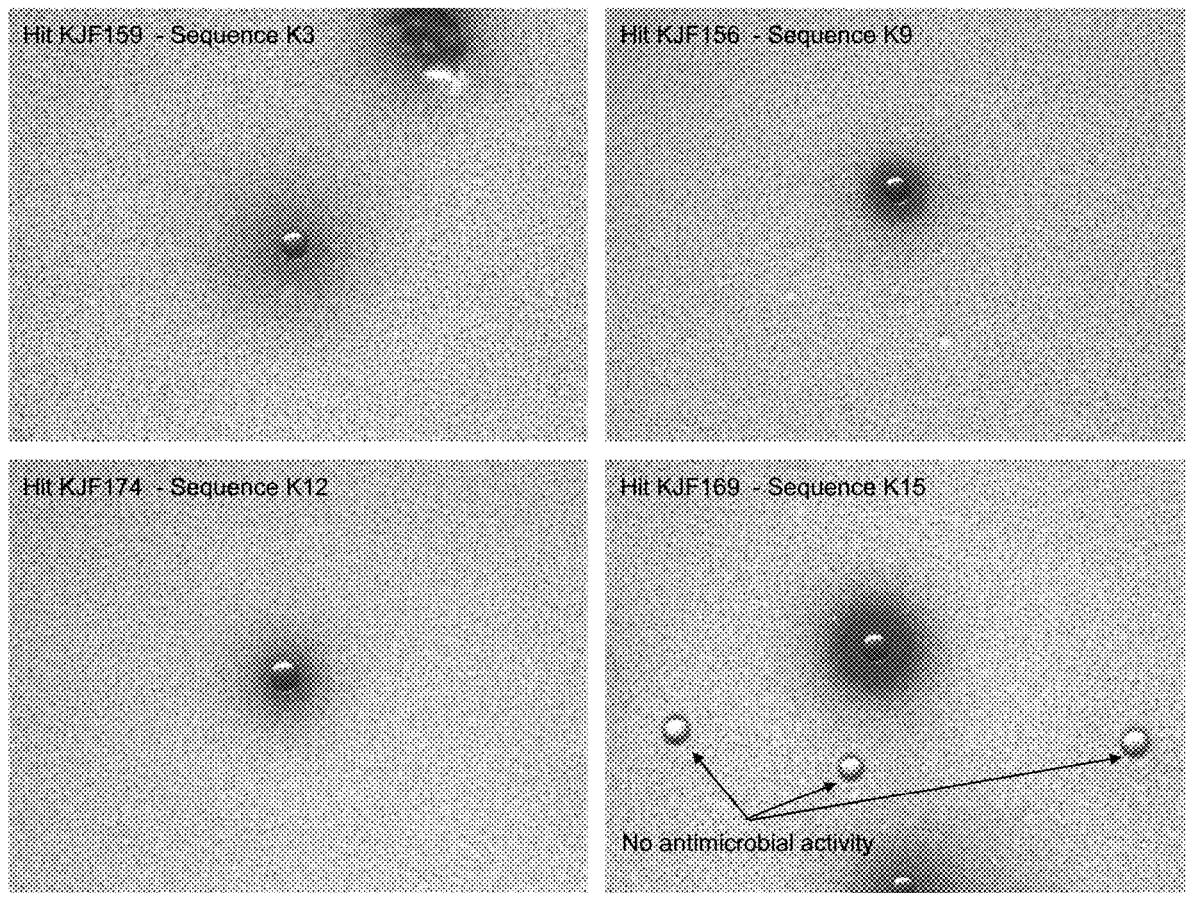
FIG. 21 shows representative images from screening of the PLAD linked proof-of-concept library. Easily visible zones of inhibition are observed around beads releasing peptoids with varying degrees of antimicrobial activity. Beads releasing peptoids from the library with no antimicrobial activity can be observed in the lower right image.
Figure 22:
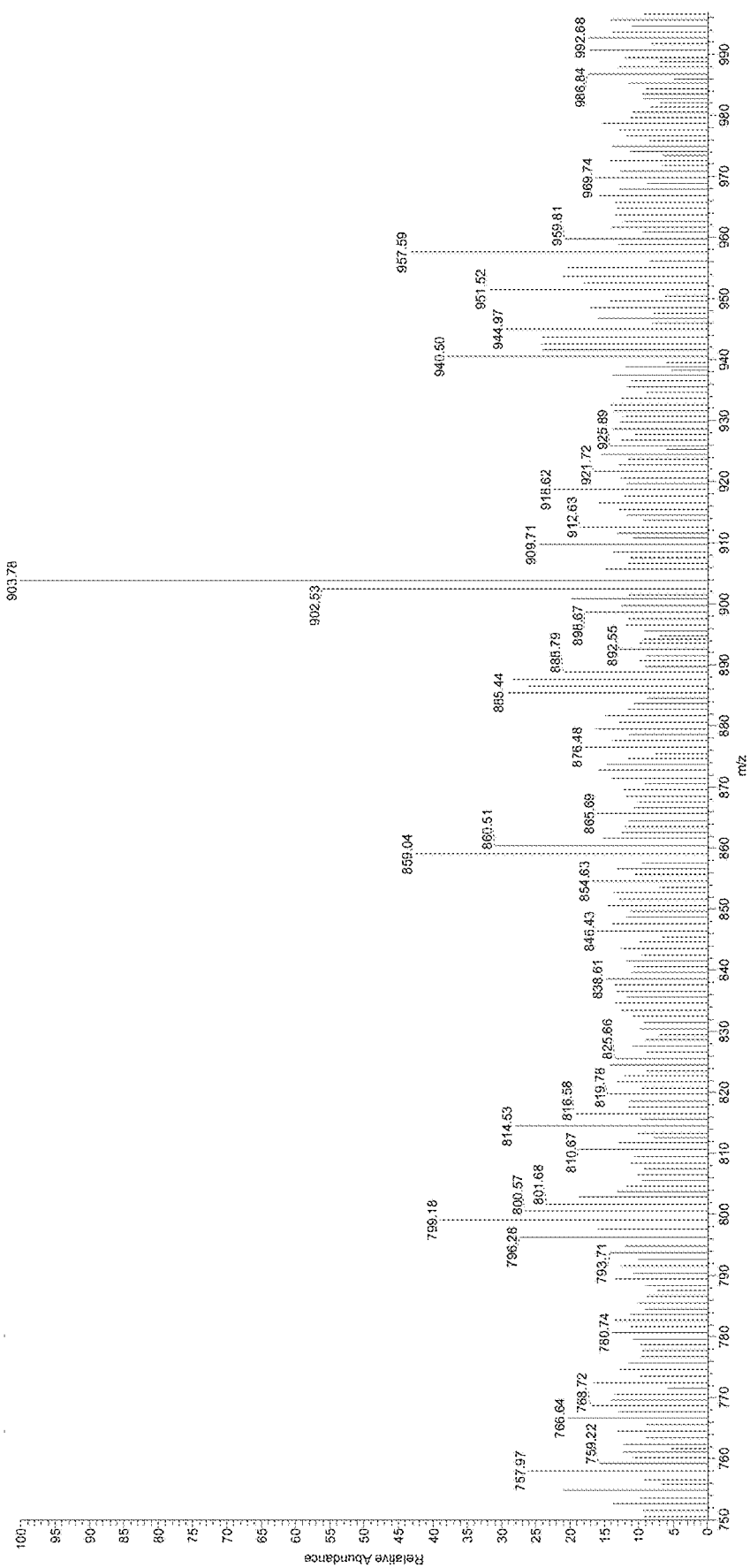
FIG. 22 is a linear MS of the α-compound of a peptoid hit identified from the proof-of-concept library screening. With a molecular weight of 903 da, this hit was identified as sequence K15.
Figure 23:
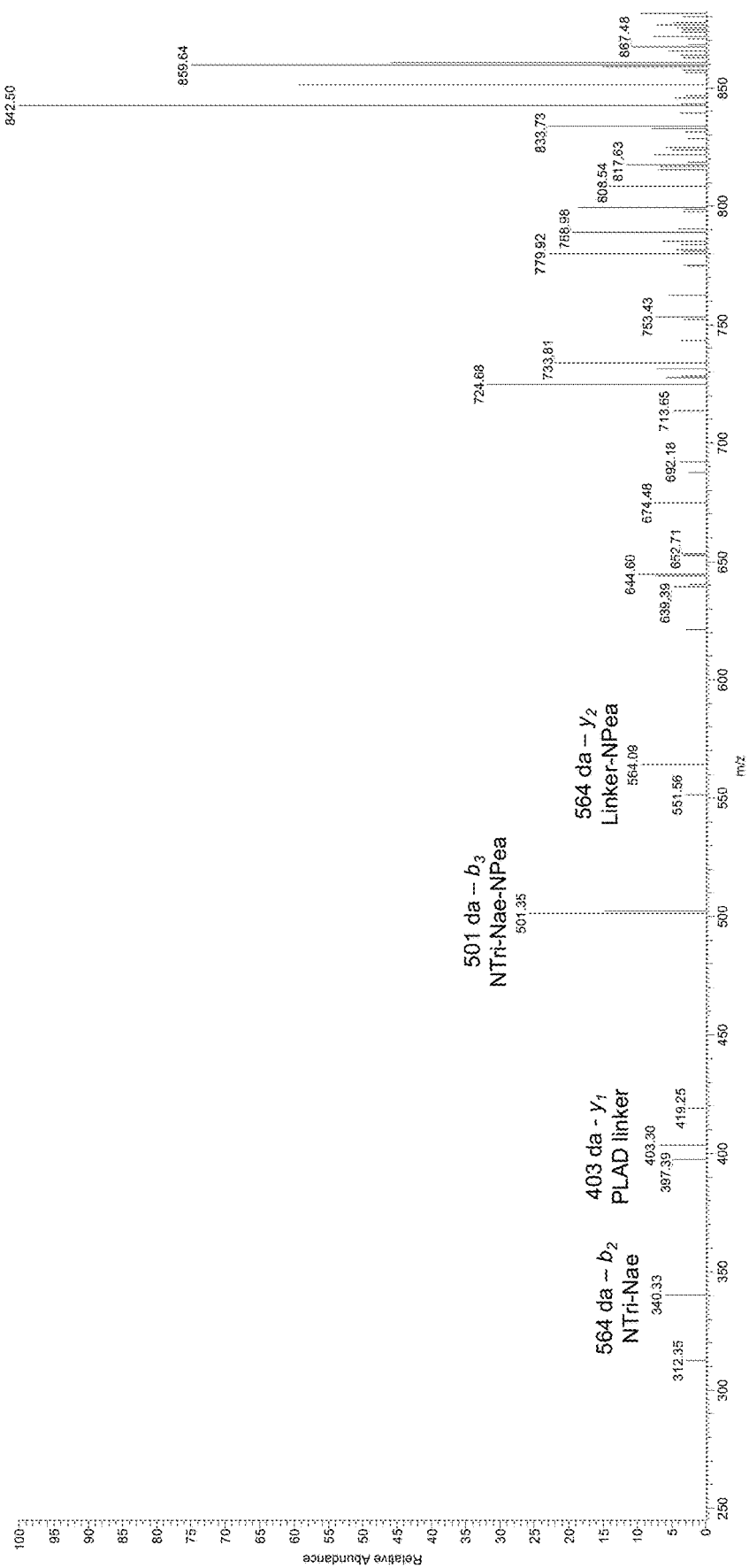
FIG. 23 is a tandem MS of the α-compound of a peptoid hit identified as K15 during linear MS analysis. They and b ions successfully identified are shown and confirm the sequence of this peptoid as K15.

This library was screened against nonpathogenic *E. coli.* (ATCC 25922) as described previously with the known $C13_{4mer}$ antimicrobial peptoid and zones of inhibition were measured using a Leica M165FC microscope. In total, roughly 800 beads were screened, representing 44 replicates of the theoretical diversity. Multiple replicates were evaluated in one screening to gain a better understanding of antimicrobial peptoid sequence homology and to give statistical credence to the relationship between peptoid sequence and zone of inhibition. Representative images from this screening can be seen in FIG. 21. Hits, defined as beads with a measurable zone of inhibition, were isolated manually with surgical tweezers and placed into individual tubes. These beads were boiled in 1% sodium dodecyl sulfate (SDS) to remove bacterial and media debris from the beads. The alpha-compound of the peptoid was cleaved from the bead using cyanogen bromide then analyzed by MS and MS/MS to identify the structure of the unknown peptoid. Representative spectra are given in FIGS. 22 and 23. In total 34 hits were identified (24% hit rate) and 31 sequences were successfully obtained by MS and MS/MS (FIG. 24). A homology chart was generated to determine which residues were most prevalent at particular positions in the identified hits (FIG. 25). In the first position, most antimicrobial peptoids contained benzylamine or 1-phenylethylamine in equal prevalence, while very few contained furfurylamine. There was also little difference in the abundance of diaminoethane and diaminobutane in the second position of identified hits. Interestingly, in the third position, all antimicrobial peptoids identified contained a 1-aminotridecane submonomer. Improved antimicrobial activity with a long hydrophobic residue in this position is not surprising given previously published results. The size of the zone of inhibition, presumably a measure of the peptoid's antimicrobial potency, was also correlated with peptoid sequence (FIG. 10B). The peptoid with the largest average zone of inhibition was sequence K15 (NTri-Nae-NPea). Note that all but one of the hits identified from this screening had a larger zone of inhibition than C134mer, demonstrating the ability of even a small peptoid library in identifying potent antimicrobial agents. Interestingly, the hits with the smallest zones of inhibition correlated to those containing furfurylamine in position 1, confirming the homology data which showed very little prevalence of this submonomer in identified hits.

Figure 26:
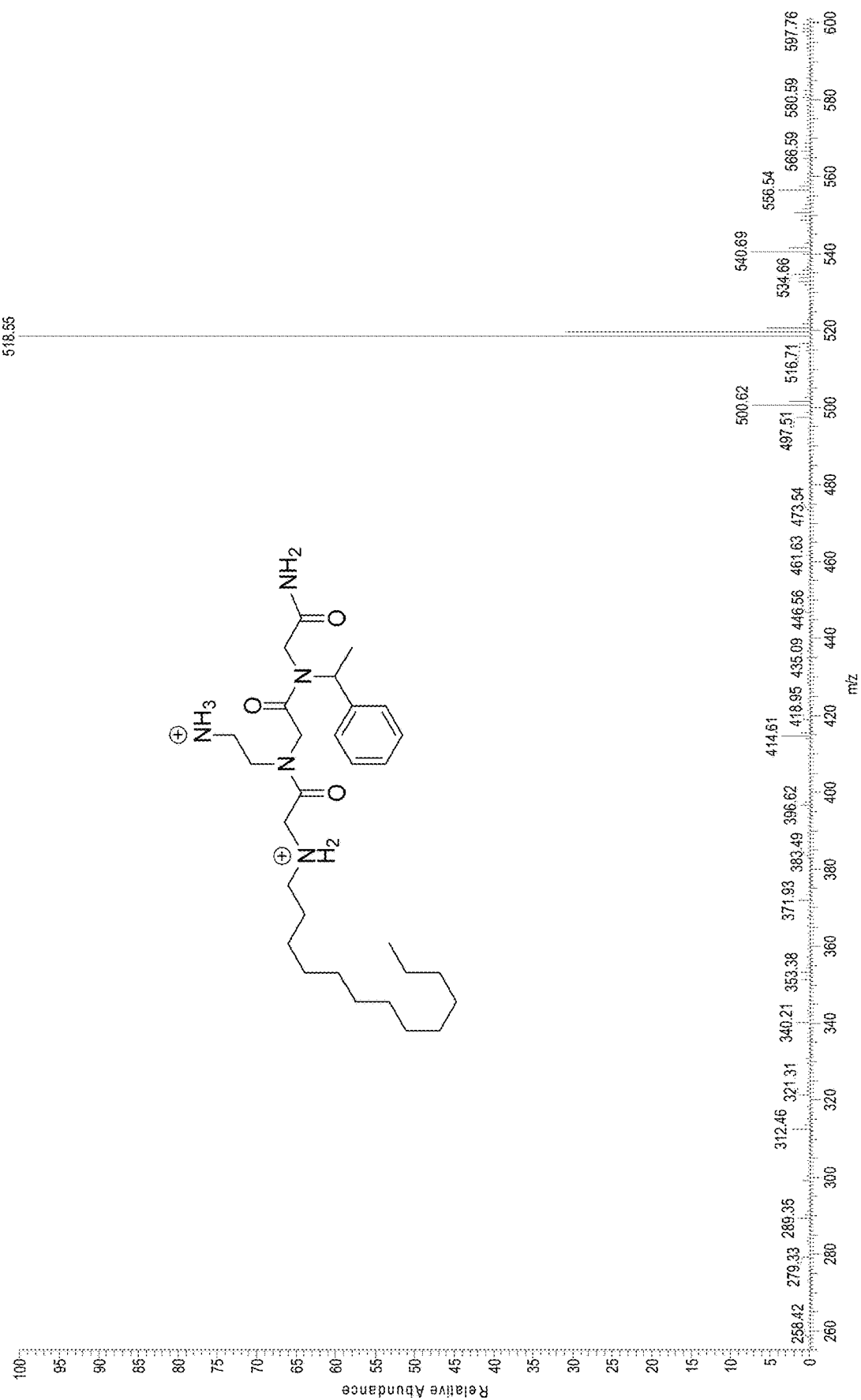
FIG. 26 shows the structure and linear MS of K15

To evaluate the efficacy of an antimicrobial peptoid identified from the PLAD Assay, the tripeptoid K15 (FIG. 26) was synthesized and its MIC against the ESKAPE pathogens determined (FIG. 10C). The ESKAPE pathogens (*Enterococcus faecium, Enterococcus faecalis, Staphylococcus aureus, Klebsiella pneumoniae, Acinetobacter baumannii, Pseudomonas aeruginosa,* and *Enterobacter* spp.) represent a cohort of bacteria that are resistant to most clinically used antibiotics.[30] We note that the *E. coli* tested here was the same strain of *E. coli* used during library screening (ATCC 25922). K15 displayed modest efficacy against six of the seven pathogens tested with the strongest antimicrobial efficacy against *A. baumannii* and *E. faecium* (25 µg/mL). This modest efficacy is undoubtedly due to the limited diversity of the proof-of-concept library. However, these results demonstrate the capability of the PLAD Assay to identify compounds with antimicrobial activity, even against pathogens with modes of antimicrobial resistance. Subsequent studies will focus on screening more diverse libraries via the PLAD Assay against each of the ESKAPE pathogens.

In summary, we have demonstrated a high-throughput screening system to identify antimicrobial peptoids, which we believe to be modular enough to screen any cohort of combinatorially synthesized molecules. By designing a branched linker with orthogonal chemical manipulability, we have shown that we can release the beta-compound of a peptoid using TCEP to cleave a disulfide bond during screening, producing an easily read zone of inhibition in response to effective antimicrobial peptoids, while leaving the alpha-compound still attached to the bead. MS analysis of test peptoids and a small proof-of-concept library demonstrate the feasibility of deconvoluting the alpha-compound peptoid sequence of strong antimicrobial peptoids after screening, allowing researchers to rapidly screen large cohorts of potential compounds without knowing their structure. The optimal reducing reagent conditions were determined for this assay and a proof-of-concept library was synthesized and screened, subsequently identifying K15, a peptoid with modest efficacy against the drug resistant ESKAPE pathogens. Current efforts are focused on screening more diverse peptoid libraries against both antimicrobial resistant bacterial and fungal pathogens.

Abbreviations

PLAD peptoid library agar diffusion
MDR multidrug resistant
AMR antimicrobial resistance
AMP antimicrobial peptide
BME β-mercaptoethanol
DTT dithiothrietol
TCEP tris(2-carboxyethyl)phosphine

REFERENCES CITED IN THIS EXAMPLE

1. Antimicrobial Resistance: Report on Global Surveillance. World Health Organization; France: 2014.
2. Antimicrobial Resistance: Tackling a Crisis for the Health and Wealth of Nations. The Review on Antimicrobial Resistance; London: 2014.
3. Tenover F C. Mechanisms of Antimicrobial Resistance in Bacteria. Am J Med. 2006; 119(6): S3-S10. [PubMed]
4. Blair J M A, Webber M A, Baylay A J, Ogbolu D O, Piddock L J V. Molecular mechanisms of antibiotic resistance. Nat Rev Microbiol. 2015; 13:42-51. [PubMed]
5. Brogden. Antimicrobial peptides: pore formers or metabolic inhibitors in bacteria? Nat Rev Microbiol. 2005; 3:238-250. [PubMed]
6. Zasloff M. Antimicrobial peptides of multicellular organisms. Nature. 2002; 415(6870):389-95. [PubMed]
7. Jenssen Hv, Hamill P, Hancock R E W. Peptide Antimicrobial Agents. Clin Microbiol Rev. 2006; 19(3):491-511. [PMC free article] [PubMed]
8. Hancock R E, Sahl H G. Antimicrobial and host-defense peptides as new anti-infective therapeutic strategies. Nat Biotechnol. 2006; 24(12):1551-7. [PubMed]
9. Culf A S, Ouellette R J. Solid-phase synthesis of N-substituted glycine oligomers (alpha-peptoids) and derivatives. Molecules. 2010; 15(8):5282-335. [PubMed]
10. Giuliani A, Rinaldi A C. Beyond natural antimicrobial peptides: multimeric peptides and other peptidomimetic approaches. Cell Mol Life Sci. 2011; 68(13):2255-66. [PubMed]

11. Zuckermann R N, Kerr J M, Kent S B H, Moos W H. Efficient method for the preparation of peptoids [oligo(N-substituted glycines)] by submonomer solid-phase synthesis. J Am Chem Soc. 1992; 114(26): 10646-10647.
12. Chongsiriwatana N P, Wetzler M, Barron A E. Functional synergy between antimicrobial peptoids and peptides against Gram-negative bacteria. Antimicrob Agents Chemother. 2011; 55(11):5399-402. [PMC free article] [PubMed]
13. Kapoor R, Eimerman P R, Hardy J W, Cirillo J D, Contag C H, Barron A E. Efficacy of antimicrobial peptoids against *Mycobacterium tuberculosis*. Antimicrob Agents Chemother. 2011; 55(6):3058-62. [PMC free article] [PubMed]
14. Kapoor R, Wadman M W, Dohm M T, Czyzewski A M, Spormann A M, Barron A E. Antimicrobial peptoids are effective against *Pseudomonas aeruginosa* biofilms. Antimicrob Agents Chemother. 2011; 55(6):3054-7. [PMC free article] [PubMed]
15. Chongsiriwatana N P, Patch J A, Czyzewski A M, Dohm M T, Ivankin A, Gidalevitz D, Zuckermann R N, Barron A E. Peptoids that mimic the structure, function and mechanism of helical antimicrobial peptides. Proc Natl Acad Sci USA. 2008; 105(8):2794-9. [PMC free article] [PubMed]
16. Patch J A, Barron A E. Helical peptoid mimics of magainin-2 amide. J Am Chem Soc. 2003; 125(40): 12092-3. [PubMed]
17. Hein-Kristensen L, Knapp K M, Franzyk H, Gram L. Bacterial membrane activity of alpha-peptide/beta-peptoid chimeras: influence of amino acid composition and chain length on the activity against different bacterial strains. BMC Microbiol. 2011; 11:144. [PMC free article] [PubMed]
18. Kennedy J P, Williams L, Bridges T M, Daniels R N, Weaver D, Lindsley C W. Application of Combinatorial Chemistry Science on Modern Drug Discovery. J Comb Chem. 2008; 10(3):345-354. [PubMed]
19. Lam K S, Lebl M, Krchnak V. The "One-Bead-One-Compound" Combinatorial Library Method. Chem Rev. 1997; 97(2):411-448. [PubMed]
20. Figliozzi G M, Goldsmith R, Ng S C, Banville S C, Zuckermann R N. Methods of Enzymology. Vol. 267. Academic Press; 1996. Synthesis of N-substituted glycine peptoid libraries; pp. 437-447. [PubMed]
21. Udugamasooriya D G, Dineen S P, Brekken R A, Kodadek T. A Peptoid "Antibody Surrogate" That Antagonizes VEGF Receptor 2 Activity. J Am Chem Soc. 2008; 130(17):5744-5752. [PubMed]
22. Gao Y, Kodadek T. Synthesis, Screening and Hit Optimization of Stereochemically Diverse Combinatorial Libraries of Peptide Tertiary Amides. Chem Biol. 2013; 20(3):360. [PMC free article] [PubMed]
23. Fluxa V S, Maillard N, Page M G P, Reymond J-L. Bead diffusion assay for discovering antimicrobial cyclic peptides. Chem Commun. 2011; 47(5):1434-1436. [Pubkled]
24. Oldenburg K R, Vo K T, Ruhland B, Schatz P J, Yuan Z. A Dual Culture Assay for Detection of Antimicrobial Activity. J Biomol Screening. 1996; 1(3):123-130.
25. Silen J L, Lu A T, Solas D W, Gore M A, Maclean D, Shah N H, Coffin J M, Bhinderwala N S, Wang Y, Tsutsui K T, Look G C, Campbell D A, Hale R L, Navre M, DeLuca-Flaherty C R. Screening for Novel Antimicrobials from Encoded Combinatorial Libraries by Using a Two-Dimensional Agar Format. Antimicrob Agents Chemother. 1998; 42(6):1447-1453. [PMC free article] [PubMed]
26. Chen X, Tan P H, Zhang Y, Pei D. On-Bead Screening of Combinatorial Libraries: Reduction of Nonspecific Binding by Decreasing Surface Ligand Density. J Comb Chem. 2009; 11(4):604-611. [PMC free article] [PubMed]
27. Kappel J, Barany G. Methionine anchoring applied to the solid-phase synthesis of lysine-containing "head-to-tail" cyclic peptides. Lett Pept Sci. 2003; 10(2):119-125.
28. Chongsiriwatana N P, Miller T M, Wetzler M, Vakulenko S, Karlsson A J, Palecek S P, Mobashery S, Barron A E. Short Alkylated Peptoid Mimics of Antimicrobial Lipopeptides. Antimicrob Agents Chemother. 2011; 55(1): 417-420. [PMC free article] [PubMed]
29. Mojsoska B, Zuckermann R N, Jenssen Hv. Structure-Activity Relationship Study of Novel Peptoids That Mimic the Structure of Antimicrobial Peptides. Antimicrob Agents Chemother. 2015; 59(7):4112-4120. [PMC free article] [PubMed]
30. Pendleton J N, Gorman S P, Gilmore B F. Clinical relevance of the ESKAPE pathogens. Expert Rev Anti-Infect Ther. 2013; 11(3):297-308. [PubMed]

Example 2

Synthesis and Screening Procedures

Materials and Methods

Chemicals for this project were purchased from Fisher Scientific (Waltham, Mass.), Alfa Aesar (Haverhill, Mass.), Amresco (Solon, Ohio), TCI America (Portland, Oreg.), Anaspec (Fremont, Calif.), EMD Millipore (Billerica, Mass.), Peptides International (Louisville, Ky.), and Chem-Implex (Wood Dale, Ill.). Non-pathogenic *E. coli* (ATCC 25290) were provided by Dr. Mary Farone in the Department of Biology at Middle Tennessee State University (MTSU). All mass spectra were acquired on either a Waters Synapt HDMS QToF with Ion Mobility or a Thermo Scientific LTQ XL Linear Ion Trap Mass Spectrometer and all NMR spectra were acquired on a JOEL ECA 500 NMR spectrometer. All images were acquired using a Leica M165FC stereomicroscope and images were analyzed using Adobe Photoshop and Microsoft Excel.

N-(tert-butoxycarbonyl)-cystamine

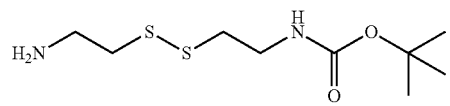

Cystamine dihydrochloride (4 g, 17.78 mmol) was dissolved in methanol (200 mL) and cooled to 0° C. Triethylamine (7.45 mL, 53.33 mmol) was added and stirred for 30 min. Boc-anhydride (4.05 mL, 17.78 mmol) was then added drop wise over 10 min and allowed to stir for 1 h. The solution was concentrated in vacuo, then washed with diethyl ether (3×30 mL). 1 M NaOH solution was added to the product and extracted 2× with $CH_2Cl_2$. Both organic layers were combined and washed 2× with $H_2O$. The organic layer was then dried over $CaCl_2$ and concentrated in vacuo to yield a white solid (3.9 g, 86% yield). ESI $[M+H]^{+1}$ expected 253.39 Da, observed 253.1 Da. $^1H$ NMR ($CDCl_3$) δ 1.45 (s, 9H), δ 2.77 (q, 4H, J=6.19 Hz), δ 3.02 (t, 4H, J=6.19 Hz), δ 3.45 (m, 2H), δ 5.02 (s, 1H).

N-(tert-butoxycarbonyl)-1,4-diaminobutane

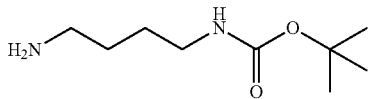

Concentrated HCl (2.85 mL, 34.09 mmol) was added to methanol (50 mL) and cooled to 0° C. on ice. 1,4-Diaminobutane (3 g, 34.09 mmol) was added to the mixture and stirred for 20 min. Water (ddH$_2$O; 7 mL) was added and stirred 30 minutes. Di-tert-butyl dicarbonate (11.72 mL, 51.11 mmol) in methanol (30 mL) was added drop wise over 10 min then stirred for 1 h. The solvent was evaporated in vacuo and the resulting solid washed with diethyl ether (3×30 mL). 1 M NaOH solution was added and the product was extracted 2× with CH$_2$Cl$_2$. Both organic layers were combined and washed 1× with a brine solution. The organic layer was then dried over CaCl$_2$ and concentrated in vacuo to yield a white solid (4.81 g, 75% yield). ESI [M+H]$^{+1}$ expected 189.27 Da, observed 189.2 Da. $^1$H NMR (500 MHz, CDCl$_3$): δ 4.61 (s, 1H), 3.13 (m, 2H), 2.17 (m, 2H), 1.50 (m, 6H), 1.44 (s, 9H).

N-(tert-butoxycarbonyl)-1,2-diaminoethane

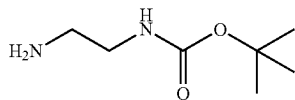

Concentrated HCl (3.89 mL, 46.6 mmol) was added to methanol (50 mL) and cooled to 0° C. on ice. 1,2-Diaminoethane (2.8 g, 46.6 mmol) was added to the mixture and stirred for 20 min. Water (ddH$_2$O; 8 mL) was added and stirred 30 minutes. Di-tert-butyl dicarbonate (16.08 mL, 70.0 mmol) in methanol (34 mL) was added drop wise over 10 min then stirred for 1 h. The solvent was evaporated in vacuo and the resulting solid washed with diethyl ether (3×30 mL). 1 M NaOH solution was added and the product was extracted 2× with CH$_2$Cl$_2$. Both organic layers were combined and washed 1× with brine. The organic layer was then dried over CaCl$_2$ and concentrated in vacuo to yield a white solid (2.92 g, 39.2% yield). ESI [M+H]$^{+1}$ expected 161.22 Da, observed 161.1 Da. $^1$H NMR (500 MHz, CDCl$_3$): δ 4.85 (s, 1H), 3.09 (m, 2H), 2.67 (q, 2H, J=6.30 Hz), 1.46 (m, 2H), 1.43 (s, 9H).

Figure 11:
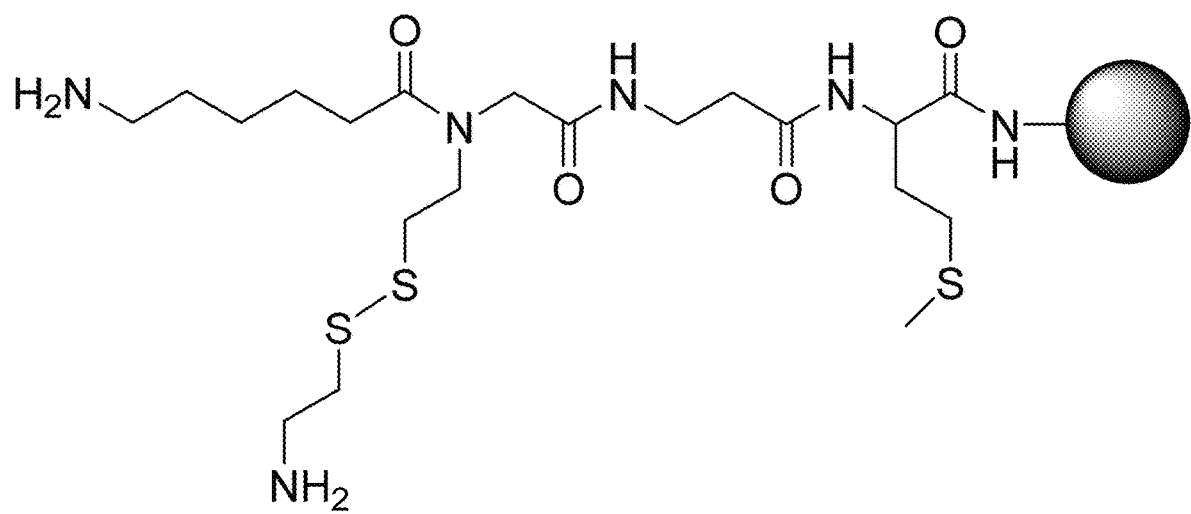
FIG. 11 shows the chemical structure of a synthesized branched disulfide linker attached to a polyethylene-grafted polystyrene bead.

Branched Disulfide Linker Synthesis (FIG. 11)

500 mg of TentaGel® macrobeads (0.25 mmol/g loading capacity) were swollen for 20 min in dimethylformamide (DMF). Fmoc-Met-OH (320 mg, 0.82 mmol, 7 eq.) was activated with N,N,N',N'-tetramethyl-O-(1H-benzotriazol-1-yl)uronium hexafluorophosphate (HBTU; 330 mg, 0.82 mmol, 7 eq.) for 10 min in 10 mL DMF with 5% N-methylmorpholine (NMM; v/v). This solution was then added to the TentaGel® resin and allowed to react for 1 h with gentle rocking. Fmoc deprotection of the methionine was accomplished using 10 mL of 20% piperidine/DMF (v/v) solution for 10 min twice. Fmoc-β-Ala-OH (270 mg, 0.87 mmol, 7 eq.) was activated with HBTU (330 mg, 0.87 mmol, 7 eq.) for 10 min in 10 mL DMF with 5% NMM (v/v), added to the resin and allowed to react for 1 h with gentle rocking. Fmoc deprotection was again accomplished with 10 mL 20% piperidine/DMF (v/v) as done before. N-(tert-butoxycarbonyl)-cystamine was next incorporated using peptoid submonomer synthesis.[1] Briefly, bromoacetic acid (1.38 g; 10 mmol) in anhydrous DMF (5 mL) was mixed with diisopropylcarbodiimide (DIC; 2.5 mL; 16 mmol) in anhydrous DMF (5 mL) and added to the resin. The reaction was then microwaved in a 1000 kW commercial microwave at 10% power (100 kW) for 15 s twice and rocked gently for 15 min. N-(tert-butoxycarbonyl)-cystamine (550 mg, 2.2 mmol, 17 eq.) was added to the resin in 8 mL anhydrous DMF, microwaved at 10% power for 15 seconds twice and rocked gently for 45 min. Fmoc-6-aminohexanoic acid (Fmoc-Aca-OH; 175 mg, 0.50 mmol, 4 eq.) was activated with HBTU (187 mg, 0.50 mmol, 4 eq.) for 10 min in 10 mL DMF, added to the resin, and allowed to react for 1 h with gentle rocking. Boc group deprotection from the cystamine side chain was then done using 10 mL of a 95% TFA/2.5% H$_2$O/2.5% triisopropylsilane (TIS) mixture for 1 h followed by washing 5× with CH$_2$Cl$_2$ and 5× with DMF. Deprotection of the remaining Fmoc group was done with 20% piperidine/DMF (v/v) followed by washing 4× with DMF. All reactions were tested with a ninhydrin color test, and after each reaction the resin was washed 4× with DMF unless stated otherwise.

Figure 12:
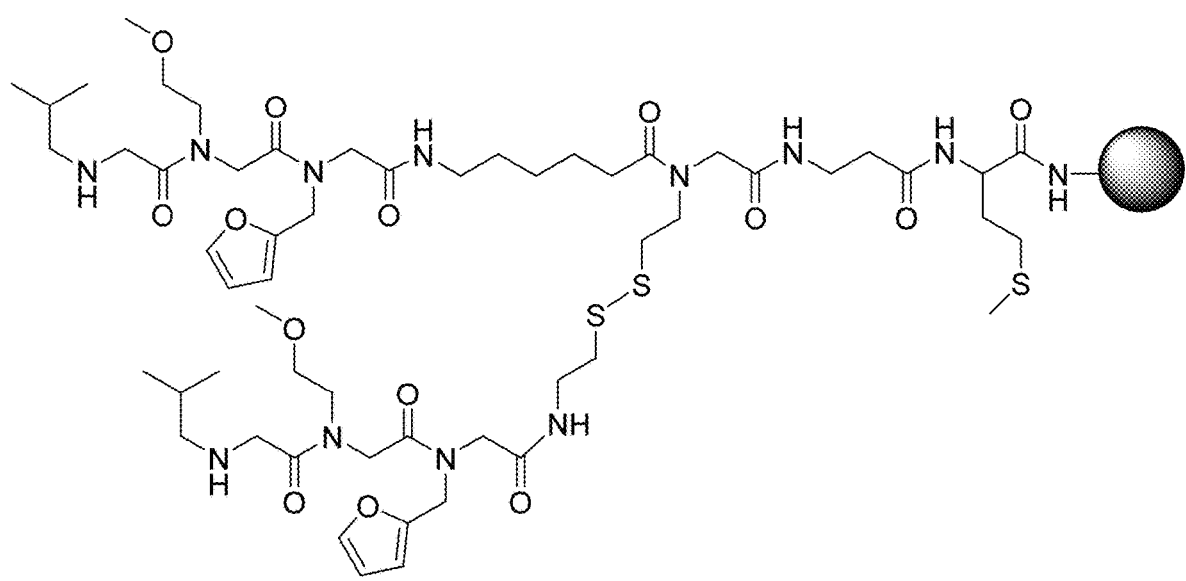
FIG. 12 shows the chemical structure of a synthesized of PLAD linked test peptoid and associated polyethylene-grafted polystyrene bead.

Synthesis of PLAD Linked Test Peptoid (FIG. 12)

Solutions of bromoacetic acid (0.417 g; 3 mmol) in anhydrous DMF (1.5 mL) and DIC (0.75 mL; 4.8 mmol) in anhydrous DMF (1.5 mL) were combined with 50 mg of resin immobilized PLAD linker. The suspended resin was microwaved twice at 10% power (100 kW) for 15 seconds, then rocked gently for 15 minutes. After the prescribed time, the mixture was aspirated and washed four times with DMF. Benzylamine (0.643 g; 6 mmol) in anhydrous DMF (3.0 mL) was added to the resin and microwaved twice at 10% power for 15 seconds followed by gentle rocking for 15 minutes. The suspension was aspirated and washed 4× with DMF. The previously described bromoacetic acid and DIC reaction was repeated. 2-methoxyethylamine (0.451 g; 6 mmol) in anhydrous DMF (3.0 mL) was added, microwaved, and rocked for 15 minutes. The suspension was then aspirated and washed 4× with DMF. Again, the bromoacetic acid and DIC coupling was repeated. Isopropylamine (0.355 g; 6 mmol) in anhydrous DMF (3.0 mL) was added to the resin, microwaved, and rocked for 15 minutes. The mixture was aspirated and washed 4× with DMF. All reactions were tested using a ninhydrin color test.

The complete test peptoid was analyzed by treating a small aliquot of resin with 75 μL of cyanogen bromide (CNBr; 40 mg/mL) in 80:20 acetonitrile (ACN):water containing 0.1 M HCl for 18 h. This solution was then removed in vacuo and the cleaved peptoid resuspended in 200 μL of 80:20 ACN:water containing 0.05% TFA and analyzed by MS. The β-compound of the test peptoid was analyzed by treating a small aliquot of resin with 500 μL of tris(2-carboxyethyl)phosphine (TCEP; 1 mM) in water for 1 h at room temperature. The resulting supernatant was then analyzed by MS. The α-compound of the peptoid was analyzed by washing the TCEP treated aliquot of resin 3× with water and subsequently treating with 75 μL CNBr (40 mg/mL) in 80:20 ACN:water containing 0.1 M HCl for 18 h. This solution was then removed in vacuo and the cleaved peptoid resuspended in 200 μL of 80:20 acetonitrile:water containing 0.05% TFA and analyzed by MS and MS/MS.

Synthesis of PLAD Linked C13$_{4mer}$ (FIG. 3)

To 150 mg of resin immobilized branched disulfide linker was added bromoacetic acid (0.414 g; 3 mmol) in anhydrous DMF (1.5 mL) and DIC (0.75 mL; 4.8 mmol) in anhydrous DMF (1.5 mL). This mixture was microwaved 2× at 10% power (100 kW) for 15 seconds, rocked gently for 15 minutes, and washed 4× with DMF. N-(tert-butoxycarbonyl)-1,4-diaminobutane (300 mg, 1.59 mmol) in anhydrous DMF (3 mL) was then added, microwaved 2× at 10% power for 15 seconds, and reacted for 30 minutes, followed by washing 4× with DMF. The bromoacetic acid and DIC step was then repeated as described above. Phenylethylamine (2 M) in anhydrous DMF (3 mL) was added, microwaved, and allowed to react for 30 minutes, after which it was washed with 4× with DMF. These procedures were then repeated with phenylethylamine and N-(tert-butoxycarbonyl)-1,4-diaminobutane again, respectively. After an additional bromoacetic acid/DIC coupling step, 1-aminotridecane (2 M) in anhydrous DMF (3 mL) was added to the resin, microwaved, and rocked gently for 50 minutes. Resin was then washed 4× with $CH_2Cl_2$ and 4× with DMF. Deprotection of remaining Boc groups was then accomplished using 8 mL of a 95% TFA/2.5% $H_2O$/2.5% TIS solution for 1 hr. Resin was then washed 5× with $CH_2Cl_2$ and 5× with DMF. All reactions were tested using a ninhydrin color test.

The complete $C13_{4mer}$ was analyzed by treating a small aliquot of resin with 75 μL of cyanogen bromide (CNBr; 40 mg/mL) in 80:20 ACN:water containing 0.1 M HCl for 18 h. This solution was then removed in vacuo and the cleaved peptoid resuspended in 200 μL of 80:20 acetonitrile:water containing 0.05% TFA and analyzed by MS. The β-compound of the test peptoid was analyzed by treating a small aliquot of resin with 500 μL of tris(2-carboxyethyl)phosphine (TCEP; 1 mM) in water for 1 h at room temperature. The resulting supernatant was then analyzed by MS.

Reducing Reagent Optimization

Solid lysogeny broth (LB) was autoclaved at 121° C. and agar plates (10 mL) were poured and kept at room temperature overnight to dry them of excess condensation. The solid agar was plated first to serve as a support to be overlaid with soft agar, allowing for a smooth, thin layer for the peptoid modified TentaGel® resin to be dispersed in. Overnight culture was prepared in LB broth (5 mL) by inoculating with ATCC 25922 *E. coli* frozen stock and incubating at 37° C. for 20 h. TentaGel® beads functionalized with PLAD linked $C13_{4mer}$ were washed 2× with $H_2O$ then allowed to equilibrate overnight in $H_2O$. Soft agar for overlay was heated to 100° C. for 30 minutes and cooled to 47° C., which kept it liquid. Compound beads were then equilibrated in 500 μL phosphate-buffer saline (PBS; pH 7.2), for each plate, for 30 minutes. Soft agar (3 mL), 75 μL of *E. coli* overnight culture, and PLAD linked $C13_{4mer}$ beads in PBS solution (500 μL) were then combined, and inverted 6-7 times gently to avoid air bubbles. This mixture, serving as the negative control with no reducing reagent, was then poured onto a hard agar plate and spread evenly into a thin layer by manual agitation. Dithiothreitol (DTT), 2-mercaptoethanol (BME), and tris(2-carboxyethyl)phosphine (TCEP) were then tested at varying concentrations to determine effectiveness at releasing the peptoid β-compound from the bead while maintaining good bacterial growth. Stock solutions of 100 mmol/L DTT, BME, and TCEP were prepared in PBS (pH 7.2). Each reducing agent was tested as described above by addition of the appropriate amount of stock reagent to separate individual plates. Final concentrations of reducing reagent in the soft agar overlay mixture 2, 4, 10, and 14 mmol/L for all three reducing agent. All plates were then allowed to solidify and incubated at 37° C. for 18 hours. Zones of inhibition, defined as the distance between the edge of a bead and the beginning of bacterial growth near that bead, were measured using a Leica M165FC microscope. Images were also analyzed by Adobe Photoshop to gain a measure of bacterial lawn density by measuring the light reflected off of the bacterial lawn when illuminated at an angle. Both sets of analyses, zone of inhibition measurements and bacterial lawn density measurements were performed on the same plates; bacterial lawn density was measured in areas of the plate where beads were not found.

Proof-of-Concept Library Synthesis (FIGS. 25A and 25B)

To 100 mg of resin modified with branched disulfide linker was equilibrated in anhydrous DMF and bromoacetic acid (0.414 g; 3 mmol) in anhydrous DMF (1.5 mL) and DIC (0.75 mL; 4.8 mmol) in anhydrous DMF (1.5 mL) were added. This mixture was microwaved 2× at 10% power (100 kW) for 15 seconds, rocked gently for 30 minutes, and washed 4× with DMF. Anhydrous DMF (3 mL) was then added and the resin was split into three vials (1 mL each). DMF was removed from each vial and to the first was added 2 M furfurylamine in anhydrous DMF (2 mL), to the second 2 M benzylamine in anhydrous DMF (2 mL), and to the third 2 M phenylethylamine in anhydrous DMF (2 mL). All three vials were then microwaved 2× at 10% power (100 kW) for 15 seconds and rocked gently for 30 minutes. The resin from the three vials was then pooled together and washed 4× with DMF and equilibrated in anhydrous DMF. Bromoacetic/DIC coupling was then done for 30 minutes and the resin was washed 4× with DMF. Anhydrous DMF (2 mL) was added, and the resin was split into two vials (1 mL each). DMF was removed from both vials and to the first vial N-(tert-butoxycarbonyl)-1,4-diaminobutane (700 mg, 1.85 M) in anhydrous DMF (2 mL) was added, and to the second vial N-(tert-butoxycarbonyl)-1,2-diaminoethane (550 mg, 1.80 M) in anhydrous DMF (2 mL) was added. Both vials were microwaved 2× at 10% power (100 kW) for 15 seconds and rocked gently for 30 minutes. The two vials were combined and washed 4× with DMF, then equilibrated in anhydrous DMF. Bromoacetic/DIC coupling was then done for 30 minutes and the resin was washed with DMF 4×. Anhydrous DMF (3 mL) was then added to the resin and split into three separate vials. The DMF was removed and to the first vial 2 M isopropylamine in anhydrous DMF (2 mL) was added, to the second vial 2 M 1-aminodecane in anhydrous DMF (2 mL) was added, and to the third vial 2 M 1-aminotridecane in anhydrous DMF (2 mL) was added. These amine coupling vials were microwaved 2× at 10% power (100 kW) for 15 seconds and rocked gently for 30 minutes. Vials were then pooled and washed 4× with DMF and 4× with $CH_2Cl_2$. Deprotection of Boc groups was accomplished using 8 mL 95% TFA/2.5% $H_2O$/2.5% TIS solution for 1 hour. Resin was washed 5× with $CH_2Cl_2$ followed by 5× with DMF. This semi-combinatorial synthesis resulted in 18 unique peptoid sequences immobilized on the PLAD linker system for proof-of-concept testing. Ninhydrin tests were done following each successive bromoacetic acid step and pooling of amines to show confirm successful coupling.

Proof-of-Concept Library Screening

Solid lysogeny broth (LB) was autoclaved at 121° C. and agar plates (10 mL) were poured and kept at room temperature overnight to dry them of excess condensation. The solid agar was plated first to serve as a support to be overlaid with soft agar, allowing for a smooth, thin layer for the peptoid modified TentaGel® resin to be dispersed in. Overnight culture was prepared in LB broth (5 mL) by inoculating with ATCC 25922 *E. coli* frozen stock and incubating at 37° C. for 20 h. Three aliquots of resin (4 mg) functionalized with PLAD linked proof-of-concept library were washed 2× with $H_2O$ then allowed to equilibrate overnight in $H_2O$. Soft agar for overlay was heated to 100° C. for 30 minutes and cooled to 47° C., which kept it liquid. The resin aliquots were then equilibrated in 500 μL phosphate-buffer saline (PBS; pH 7.2) for 30 minutes. Soft agar (3 mL), 75 μL of E. coli overnight culture, 500 μL of TCEP (100 mM stock; 14 mM final) and resin in PBS (500 μL) were then combined, and inverted 6-7 times gently to avoid air bubbles. This mixture was then poured onto a hard agar plate and spread evenly into a thin layer by manual agitation. All plates were then allowed to solidify and incubated at 37° C. for 18 hours. Zones of inhibition, defined as the distance between the edge of a bead and the beginning of bacterial growth near that bead, were measured using a Leica M165FC microscope. Hits, defined as beads with a measurable zone of inhibition, were isolated manually with surgical tweezers and placed into individual tubes. These beads were boiled in 1% sodium dodecylsulfate (SDS) for 1 hour and washed 4× with water. The alpha compound of the peptoid was cleaved from the bead using cyanogen bromide (50 μL; 40 mg/mL) in 80:20 acetonitrile:water containing 0.1 M HCl for 18 hours in the dark. This solution was then removed in vacuo and the cleaved peptoid resuspended in 80:20 acetonitrile:water containing 0.05% TFA. MS and MS/MS analysis was then done as previously described to identify the structure of the unknown peptoid. In total 34 hits were identified (24% hit rate) and 31 sequences were successfully obtained by MS and MS/MS.

Synthesis of K15 Peptoid

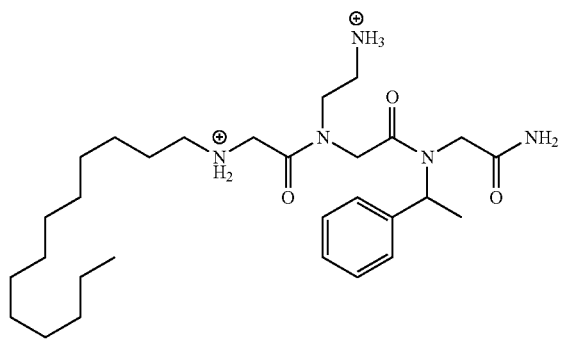 [SMILES: CCCCCCCCCCCCC[NH2+]CC(=O)N(CC[NH3+])CC(=O)N(CC(N)=O)C(C)c1ccccc1]

Rink Amide resin (0.101 g; 0.38 mmol/g loading) was swollen in DMF for 20 minutes. After removing the DMF, 20% piperidine in DMF (5 mL) was added to the resin and rocked for 30 minutes. The piperidine solution was drained, and the beads were washed 3× with DMF. The piperidine deprotection step was once more repeated, and the resin washed 3× with DMF. Solutions of bromoacetic acid (0.417 g; 3 mmol) in anhydrous DMF (1.5 mL) and DIC (0.75 mL; 4.8 mmol) in anhydrous DMF (1.5 mL) were combined with the deprotected Rink Amide beads. The resin was microwaved twice at 10% power (100 kW) for 15 seconds, then rocked gently for 15 minutes; after which, the mixture was aspirated and washed four times with DMF. 2-phenylethylamine (0.364 g; 3 mmol) in anhydrous DMF (3.0 mL) was added to the resin and microwaved twice at 10% power for 15 seconds followed by gentle rocking for 30 minutes. The suspension was aspirated and washed 4× with DMF. The previously described bromoacetic acid and DIC reaction was repeated. Boc-ethylene diamine (0.486 g; 3 mmol) in anhydrous DMF (3.0 mL) was added, microwaved, and rocked for 30 minutes. The suspension was then aspirated and washed 4× with DMF. Again, the bromoacetic acid and DIC coupling was repeated. Tridecylamine (0.598 g; 3 mmol) in anhydrous DMF (3.0 mL) was added to the resin, micro- waved, and rocked for 40 minutes. The mixture was aspirated and washed 4× with DMF and 4× with $CH_2Cl_2$. A ninhydrin test was performed on a small sample after every coupling. The tripeptoid was cleaved from the resin by treating 2× with TFA:water:TIS (95:2.5:2.5) for 1 h each. TFA was removed by bubbling with air and residual substance resuspended in 1:1 water:acetonitrile containing 0.05% TFA. K15 was then purified by reverse phase HPLC using a C18 column and a gradient of water with 0.05% TFA to acetonitrile with 0.05% TFA. The identity of the compound was confirmed by MS and the solvent removed under vacuum to provide pure K15 (17 mg; 17% yield).

K15 MIC Testing in ESKAPE Pathogens

Peptoid K15 was analyzed via a traditional broth minimum inhibitor concentration (MIC) assay against seven different ESKAPE pathogens (Acinetobacter baumanii, ATCC 19606; Enterococcus faecalis, ATCC 29212; Enterococcus faecium, ATCC 19434; Escherichia coli, ATCC 25922; Klebsiella pneumoniae, ATCC 700603; Pseudomonas aeruginosa, ATCC 27853; Staphylococcus aureus, ATCC 29213). For each of the bacterial strains screened in the ESKAPE panel, 1-3 isolated colonies were collected from a TSA plate by a flame sanitized wire loop and resuspended in 5 mL of TSB. The solutions were incubated at 37° C. for 18-24 hours. After the growth period, the turbidity was measured at 600 nm and adjusted to an optical density of 0.08-0.13 by diluting with TSB for an approximate concentration of $1 \times 10^8$ CFU/mL. Once the desired OD was achieved, 20 μL of the bacteria suspension were diluted 1:20 in 380 μL Cation Adjusted Mueller-Hinton broth (CAMHB) for a final concentration of $5 \times 10^6$ CFU/mL.

4 μL of a 10 mM stock of K15 were diluted in 356 μL CAMHB for each bacterial strain assayed (a total of 28 μL stock in 2.478 mL broth for ESKAPE panel). 180 μL of this solution were delivered to three wells. For each dilution to be studied, 90 μL of the 100 μM solution were withdrawn and delivered to 90 μL of broth This 1:2 serial dilution was continued to give final K15 concentrations of 100, 50, 25, 12.5, 6.3, 3.1, and 1.6 μM. 90 μL of the final triplicate set being removed such that each well has a volume of 90 μL. A negative control containing 90 μL of broth with no K15 was also prepared. 10 μL of the 1:20 diluted bacteria were added to each well for a total volume of 100 μL. 100 μL of broth were delivered to a well in triplicate to serve as a media control. A tetracycline control was used, composed of 4 μL 2 mg/mL antibiotic in 356 μL broth with 40 μL bacteria. 100 μL of this solution were delivered to each of three wells.

The prepared plates were incubated for another 18-24 hours. Their respective absorbance at 600 nm was analyzed on a SpectraMax M5 Plate Reader. 10 μL of PrestoBlue were added to each well and allowed to incubate for an hour. Absorbance at 555, 570, and 585 nm was analyzed to determine viable cells having survived treatment by the antimicrobial compound. This assay, which utilizes triplicates of each K15 concentration, was ran in duplicate or triplicate for each microorganism tested on different days.

REFERENCES CITED IN THIS EXAMPLE

1. Zuckermann, R. N.; Kerr, J. M.; Kent, S. B. H.; Moos, W. H., Efficient method for the preparation of peptoids [oligo (N-substituted glycines)] by submonomer solid-phase synthesis. Journal of the American Chemical Society 1992, 114, (26), 10646-10647.

Equivalents

Those skilled in the art will recognize, or be able to ascertain, using no more than routine experimentation, numerous equivalents to the specific substances and procedures described herein. Such equivalents are considered to be within the scope of this invention, and are covered by the following claims.

Although not to be interpreted as exclusive, specific equivalents include the following. In embodiments, the pathogen or cells of interest that are inoculated within the growth media may be prokaryotic cells, eukaryotic cells, or any organism that can grow on any type of growth media. For instance, in addition to the use of microorganisms discussed above, the cells of interest may be mammalian cells. Furthermore, peptoids are only one of many compounds that may be tethered to the branched linker system in the disclosed assay. Alternate compounds that may be tethered to the branched linker system of the present invention include, but are not limited to utilized in the solid supported branched linker assay system may be small molecules, peptides, DNA/RNA aptamers, or antimicrobial peptides.

What is claimed:

1. A solid supported branched linker assay system, comprising:
   a.) an alpha compound and a beta compound, wherein the alpha compound and the beta compound are each reversibly tethered to a solid support;
   b.) a branched linker that is coupled to the solid support and tethers the alpha and beta compounds to the solid support;
   c.) the branched linker further comprising two cleavable linkers that are chemically distinct from one another, wherein a first chemically distinct linker tethers the beta compound to the branched linker and a second chemically distinct linker tethers the alpha compound to the branched linker;
   d.) two means for cleaving the chemically distinct linkers, wherein a first cleavage means is configured to selectively cleave the first chemically distinct linker and a second cleavage means is configured to selectively cleave the second chemically distinct linker; and
   (e) a growth medium inoculated with at least one microorganism of interest.

2. The solid supported branched linker assay system of claim 1, wherein the solid support is a polyethylene-grafted polystyrene bead.

3. The solid supported branched linker system of claim 1, wherein the alpha or beta compounds comprise peptides or antimicrobial peptides.

4. The solid supported branched linker assay system of claim 1, wherein the alpha and beta compounds are identical or the alpha compound is configured to encode for a compound that is identical to the beta compound.

5. The solid supported branched linker assay system of claim 1, wherein the alpha or beta compounds are peptoids.

6. The solid supported branched linker assay system of claim 1, wherein:
   a.) the first chemically distinct linker comprises a disulfide;
   b.) the first cleavage means comprises a reducing agent;
   c.) the second chemically distinct linker comprises a methionine; and
   d.) the second cleavage means comprises cyanogen bromide.

7. The solid supported branched linker assay system of claim 1, comprising a means for screening the therapeutic effectiveness of the beta compound and a means for identifying the alpha compound, the means for screening the therapeutic effectiveness of the beta compound comprising:
   a.) the growth medium inoculated with the at least one microorganism of interest;
   b.) the growth medium further comprising the alpha and beta compounds and the first cleavage means;
   wherein the growth medium is configured to permit growth of the microorganism of interest and, in the presence of the first cleavage means, the beta compound comprises a cleaved beta compound that is free to interact with the microorganism of interest; and
   c.) the beta compound comprising a therapeutically effective compound if a halo of inhibited cell growth surrounds the cleaved beta compound.

8. The solid supported branched linker assay system of claim 7, wherein the growth medium is soft agar.

* * * * *